US010920267B1

United States Patent
Benner et al.

(10) Patent No.: US 10,920,267 B1
(45) Date of Patent: Feb. 16, 2021

(54) ISOTHERMAL AMPLIFICATION OF OLIGONUCLEOTIDES

(71) Applicants: Steven A Benner, Gainesville, FL (US); Ozlem Yaren, Gainesville, FL (US); Patricia Moussatche, Gainesville, FL (US)

(72) Inventors: Steven A Benner, Gainesville, FL (US); Ozlem Yaren, Gainesville, FL (US); Patricia Moussatche, Gainesville, FL (US)

( * ) Notice: Subject to any disclaimer, the term of this patent is extended or adjusted under 35 U.S.C. 154(b) by 501 days.

(21) Appl. No.: 15/826,126

(22) Filed: Nov. 29, 2017

Related U.S. Application Data

(63) Continuation of application No. 14/613,960, filed on Feb. 4, 2015, now Pat. No. 10,106,837.

(60) Provisional application No. 62/427,868, filed on Nov. 30, 2016, provisional application No. 61/935,921, filed on Feb. 5, 2014.

(51) Int. Cl.
*C12Q 1/68* (2018.01)
*C12Q 1/6806* (2018.01)
*C12N 15/10* (2006.01)

(52) U.S. Cl.
CPC ......... *C12Q 1/6806* (2013.01); *C12N 15/101* (2013.01)

(58) Field of Classification Search
None
See application file for complete search history.

(56) References Cited

U.S. PATENT DOCUMENTS

| | | | |
|---|---|---|---|
| 8,691,292 B2 * | 4/2014 | Daigle | A01N 25/02 424/725 |
| 10,724,091 B1 * | 7/2020 | Meagher | C12Q 1/6853 |
| 2013/0171643 A1 | 7/2013 | Kubota | |
| 2016/0076083 A1 * | 3/2016 | Ellington | C12Q 2527/101 506/9 |

OTHER PUBLICATIONS

Kubota et al. (Biological Engineering Transactions, 2011, 4(2):81-100) (Year: 2011).*
Hong et al. (J of Clin Microbiol, 2004, p. 1956-1961) (Year: 2004).*
Tanner et al. (Biotechniques, 2012, 53:81-89) (Year: 2012).*
Hoshika et al. (Agnew Chem Int Ed, 2010, 49, 5554-5557) (Year: 2010).*
Thekisoe et al. (Am J Trop Med Hyg, 2010, 82(5):855-860) (Year: 2010).*
Saiki, Primer-directed enzymatic amplification of DNA with a thermostable DNA polymerase. Science 239, 487-491.

(Continued)

*Primary Examiner* — Stephanie K Mummert

(57) ABSTRACT

Processes are disclosed that create derivative DNA molecules in large numbers under isothermal conditions, where amplification of a looped structure derived from a target is achieved by a process that separately or in combination includes (a) a displaceable probe that (b) may be captured in a separate site, optionally containing (c) components of an artificially expanded genetic information system, where the primers optionally contain (d) components of a self-avoiding molecular recognition system, and optionally (e) involving direct transfer of DNA or RNA from a sample from a capture medium with immobilized quaternary ammonium salts.

40 Claims, 20 Drawing Sheets

Specification includes a Sequence Listing.

(56) References Cited

OTHER PUBLICATIONS

Piepenburg, DNA Detection using recombination proteins. PLoS Biol 4 (7): e204.

Tong, Multiple strategies to improve sensitivity, speed and robustness of isothermal nucleic acid amplification for rapid pathogen detection. BMC Biotechnol. 11 Art. No: 50.

Lemieux, Near instrument-free, simple molecular device for rapid detection of herpes simplex viruses: Expert Review Molec. Diagnostics 12, 437-443 DOI: 10.1586/ERM.12.34.

Yaren, A norovirus detection architecture based on isothermal amplification and expanded genetic systems. J. Virol. Methods 237, 64-71.

Kubota, Fret-based assimilating probe for sequence-specific real-time monitoring of loop-mediated isothermal amplification (LAMP). Biol. Eng. Trans. 4, 81-100.

Tanner, Simultaneous multiple target detection in real-time loop-mediated isothermal amplification. BioTechniques 53, 81-89.

Hoshika, Artificial genetic systems. Self-avoiding DNA in PCR and multiplexed PCR. Angew. Chem. Int. Edit. 49, 5554-5557.

Yaren, Standard and AEGIS nicking molecular beacons detect amplicons from the Middle East Respiratory Syndrome coronavirus, J. Virol. Methods 236, 54-61.

Yaren, Point of sampling detection of Zika virus within a multiplexed kit capable of detecting dengue and chikungunya. BMC Infect. Diseases 17.1, 293.

Nagamine, Accelerated reaction by loop-mediated isothermal amplification using loop primers. Mol. Cell. Probes, 16, 223-229.

Benner, Alternative Watson-Crick synthetic genetic systems. Synthetic Biology. Cold Spring Harbor Perspectives in Biology, Cold Spring Harbor Press. PMID: 27663774.

Wang, Biophysics of artificially expanded genetic information systems. Thermodynamics of DNA duplexes containing matches and mismatches involving 2-amino-3-nitropyridin-6-one (Z) and imidazo[1,2-a]-1,3,5-triazin-4(8H)one (P) ACS Synth. Biol. 6, 782-792.

Yang, Preparation of cationic waste paper and its application in poisonous dye removal. Water Sci. Technol. 67, 2560-2567 PMID: 23752389.

Sheng, Design of a novel molecular beacon. Modification of the stem with artificially genetic alphabet. Chem. Comm. (41), 5128-5130.

Salo, Effect of acid pH, salts, and temperature on the infectivity and physical integrity of enteroviruses. Arch. Virol. 52, 269-282.

Hanaki, Detection of murine norovirus by reverse transcription loop-mediated isothermal amplification. J. Virol. Methods 204, 17-24.

Zhu, Identification of Immune and Viral Correlates of Norovirus Protective Immunity through Comparative Study of Intra-Cluster Norovirus Strains. PLoS Pathog. 9, e1003592.

* cited by examiner

SEQUENCE LISTING

<160> NUMBER OF SEQ ID NOS: 63

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
tctgacctat cagcttttg                    19

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
aattccyayc attccaattr c                  21

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
ccccgttacc cgtcatag                      18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
gcaggcgcgt aaattacc                      18

<210> SEQ ID NO 5
<211> LENGTH: 41
<212> TYPE: DNA

<213> ORGANISM: Artificial Sequence
<220> FEATURE:
<223> OTHER INFORMATION: Synthetic

<400> SEQUENCE: 5
ccctctccgg aatcgaactt ttttgttagg gtattgrcct a                                41

<210> SEQ ID NO 6
<211> LENGTH: 44
<212> TYPE: DNA
<213> ORGANISM: Artificial Sequence
<220> FEATURE:
<223> OTHER INFORMATION: Synthetic

<400> SEQUENCE: 6
accacatcta aggaaggcat tttttcacta cctctcttyt ttag                             44

<210> SEQ ID NO 7
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<220> FEATURE:
<221> NAME/KEY: misc_feature
<222> LOCATION: (10)..(10)
<220> FEATURE:
<221> NAME/KEY: misc_feature
<222> LOCATION: (15)..(15)
<223> OTHER INFORMATION:
    2-amino-8-(beta-D-2'-deoxyribofuranosyl)-imidazo-[1,2a]-1,3,5-tri
    azin-[8H]-4-one
<220> FEATURE:
<221> NAME/KEY: misc_feature
<222> LOCATION: (27)..(27)
<220> FEATURE:
<221> NAME/KEY: misc_feature
<222> LOCATION: (35)..(35)
<223> OTHER INFORMATION:
    2-amino-8-(beta-D-2'-deoxyribofuranosyl)-imidazo-[1,2a]-1,3,5-tri
    azin-[8H]-4-one

<400> SEQUENCE: 7
cgngtttgcn ctcanccatc cgttcantcc gtcangtcag ccccgttacc cgtcatag            58

<210> SEQ ID NO 8
<211> LENGTH: 19
<212> TYPE: DNA
<213> ORGANISM: Artificial Sequence
<220> FEATURE:
<223> OTHER INFORMATION: Syntheitc

<400> SEQUENCE: 8
ataaactatr ccractagg                                                        19

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
tgtcaatcct actcttgtc                                                        19

<210> SEQ ID NO 10

```
<211> LENGTH: 18
<212> TYPE: DNA
<213> ORGANISM: Artificial Sequence
<220> FEATURE:
<223> OTHER INFORMATION: Synthetic

<400> SEQUENCE: 10
ccccagaacc caaagact                                                   18

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
tggagcttgc ggcttaa                                                    17

<210> SEQ ID NO 12
<211> LENGTH: 41
<212> TYPE: DNA
<213> ORGANISM: Artificial Sequence
<220> FEATURE:
<223> OTHER INFORMATION: Synthetic

<400> SEQUENCE: 12
actttctcgc ttgcgctttt tccttcagtr ccytatgaga a                         41

<210> SEQ ID NO 13
<211> LENGTH: 39
<212> TYPE: DNA
<213> ORGANISM: Artificial Sequence
<220> FEATURE:
<223> OTHER INFORMATION: Synthetic

<400> SEQUENCE: 13
attgacggaa gggcaccttt tttttycccg tgttgagtc                            39

<210> SEQ ID NO 14
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (10)..(10)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (15)..(15)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (27)..(27)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
```

```
<222> LOCATION: (35)..(35)
<223> OTHER INFORMATION:
      2-amino-8-(beta-D-2'-deoxyribofuranosyl)-imidazo-[1,2a]-1,3,5-tri
      azin-[8H]-4-one

<400> SEQUENCE: 14
cgngtttgcn ctcanccatc cgttcantcc gtcangtcag ccccagaacc caaagact       58

<210> SEQ ID NO 15
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (14)..(14)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (26)..(26)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (31)..(31)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (38)..(38)
<223> OTHER INFORMATION:
      6-amino-3-(2'-deoxy)-D-ribofuranosyl)-5-nitro-1H-pyridin-2-one

<400> SEQUENCE: 15
ctgacntgac ggantgaacg gatggntgag ngcaaacncg                            40

<210> SEQ ID NO 16
<211> LENGTH: 16
<212> TYPE: DNA
<213> ORGANISM: Artificial Sequence
<220> FEATURE:
<223> OTHER INFORMATION: Synthetic

<400> SEQUENCE: 16
ggtgtagtgt gacctg                                                     16

<210> SEQ ID NO 17
<211> LENGTH: 39
<212> TYPE: DNA
<213> ORGANISM: Artificial Sequence
<220> FEATURE:
<223> OTHER INFORMATION: Synthetic

<400> SEQUENCE: 17
cgtgcagccc agaacatttt tgcaaaatga gattgagcg                             39

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
```

```
tctaagggca tcacggac                                              18

<210> SEQ ID NO 19
<211> LENGTH: 16
<212> TYPE: DNA
<213> ORGANISM: Artificial Sequence
<220> FEATURE:
<223> OTHER INFORMATION: Synthetic

<400> SEQUENCE: 19
aagggccggg aaatcg                                                16

<210> SEQ ID NO 20
<211> LENGTH: 39
<212> TYPE: DNA
<213> ORGANISM: Artificial Sequence
<220> FEATURE:
<223> OTHER INFORMATION: Synthetic

<400> SEQUENCE: 20
caacgcgtat ccttgccttt ttaatcccga ctaaatgcg                       39

<210> SEQ ID NO 21
<211> LENGTH: 17
<212> TYPE: DNA
<213> ORGANISM: Artificial Sequence
<220> FEATURE:
<223> OTHER INFORMATION: Synthetic

<400> SEQUENCE: 21
gctagctaat gaccagc                                               17

<210> SEQ ID NO 22
<211> LENGTH: 57
<212> TYPE: DNA
<213> ORGANISM: Artificial Sequence
<220> FEATURE:
<223> OTHER INFORMATION: Synthetic

<400> SEQUENCE: 22
gggtttgcgc tcagccatcc gttcagtccg tcaggtcagt ctaagggcat cacggac   57

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
ctgacctgac ggactgaacg gatggctgag cgcaaaccc                       39

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
gggtttgcgc tcagccatcc gtt                                        23

<210> SEQ ID NO 25
<211> LENGTH: 16
<212> TYPE: DNA
```

```
<213> ORGANISM: Artificial Sequence
<220> FEATURE:
<223> OTHER INFORMATION: Synthetic

<400> SEQUENCE: 25
gagactgctt gcctag                                               16

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
ctggggtctt gtcttc                                               16

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
cagttggaac ccagtcaac                                            19

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gtggaacaga gtgtggattg                                           20

<210> SEQ ID NO 29
<211> LENGTH: 41
<212> TYPE: DNA
<213> ORGANISM: Artificial Sequence
<220> FEATURE:
<223> OTHER INFORMATION: Synthetic

<400> SEQUENCE: 29
ccatggattg accaggtagt tttttcgact gatggccaat g                   41

<210> SEQ ID NO 30
<211> LENGTH: 40
<212> TYPE: DNA
<213> ORGANISM: Artificial Sequence
<220> FEATURE:
<223> OTHER INFORMATION: Synthetic

<400> SEQUENCE: 30
accactgarg acatgcttgt ttttcatgtg gtcgttytcc                     40

<210> SEQ ID NO 31
<211> LENGTH: 60
<212> TYPE: DNA
<213> ORGANISM: Artificial Sequence
<220> FEATURE:
<223> OTHER INFORMATION: Synthetic

<400> SEQUENCE: 31
cgggtttgcg ctcagccatc cgttcagtcc gtcaggtcag gtggaacaga gtgtggattg   60
```

<210> SEQ ID NO 32
<211> LENGTH: 40
<212> TYPE: DNA
<213> ORGANISM: Artificial Sequence
<220> FEATURE:
<223> OTHER INFORMATION: Synthetic

<400> SEQUENCE: 32
ctgacctgac ggactgaacg gatggctgag cgcaaacccg                          40

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
cgtcaacgta ctcctaac                                                  18

<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
acgttggctt trttttgg                                                  18

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35
agcgtcttta tccacggg                                                  18

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
aygcatcrat aatggcggg                                                 19

<210> SEQ ID NO 37
<211> LENGTH: 40
<212> TYPE: DNA
<213> ORGANISM: Artificial Sequence
<220> FEATURE:
<223> OTHER INFORMATION: Synthetic

<400> SEQUENCE: 37
gaagtttcct ttcggtgggt ttttggaaga cactytcygg                          40

<210> SEQ ID NO 38
<211> LENGTH: 39
<212> TYPE: DNA
<213> ORGANISM: Artificial Sequence
<220> FEATURE:

<223> OTHER INFORMATION: Synthetic

<400> SEQUENCE: 38
aaggagtggg aggtggattt tttcayttgg tgactgcag                    39

<210> SEQ ID NO 39
<211> LENGTH: 58
<212> TYPE: DNA
<213> ORGANISM: Artificial Sequence
<220> FEATURE:
<223> OTHER INFORMATION: Synthetic

<400> SEQUENCE: 39
cgggtttgcg ctcagccatc cgttcagtcc gtcaggtcag agcgtcttta tccacggg    58

<210> SEQ ID NO 40
<211> LENGTH: 40
<212> TYPE: DNA
<213> ORGANISM: Artificial Sequence
<220> FEATURE:
<223> OTHER INFORMATION: Synthetic

<400> SEQUENCE: 40
ctgacctgac ggactgaacg gatggctgag cgcaaacccg                   40

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41
acagcyctga atgayatgg                                          19

<210> SEQ ID NO 42
<211> LENGTH: 16
<212> TYPE: DNA
<213> ORGANISM: Artificial Sequence
<220> FEATURE:
<223> OTHER INFORMATION: Synthetic

<400> SEQUENCE: 42
gcagtttctc tcaggc                                             16

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
cacttgytgc cartcattcc                                         20

<210> SEQ ID NO 44
<211> LENGTH: 16
<212> TYPE: DNA
<213> ORGANISM: Artificial Sequence
<220> FEATURE:
<223> OTHER INFORMATION: Synthetic

<400> SEQUENCE: 44
ccatgccgya accaag                                             16

<210> SEQ ID NO 45
<211> LENGTH: 40
<212> TYPE: DNA
<213> ORGANISM: Artificial Sequence
<220> FEATURE:
<223> OTHER INFORMATION: Synthetic

<400> SEQUENCE: 45
ctggtggaar tggtgtgatt ttttgggaac cttcaaaagg         40

<210> SEQ ID NO 46
<211> LENGTH: 42
<212> TYPE: DNA
<213> ORGANISM: Artificial Sequence
<220> FEATURE:
<223> OTHER INFORMATION: Synthetic

<400> SEQUENCE: 46
gaaggayggg agggaaatag tttttttagc cctrcccaca ag         42

<210> SEQ ID NO 47
<211> LENGTH: 56
<212> TYPE: DNA
<213> ORGANISM: Artificial Sequence
<220> FEATURE:
<223> OTHER INFORMATION: Synthetic

<400> SEQUENCE: 47
cgggtttgcg ctcagccatc cgttcagtcc gtcaggtcag ccatgccgya accaag         56

<210> SEQ ID NO 48
<211> LENGTH: 40
<212> TYPE: DNA
<213> ORGANISM: Artificial Sequence
<220> FEATURE:
<223> OTHER INFORMATION: Synthetic

<400> SEQUENCE: 48
ctgacctgac ggactgaacg gatggctgag cgcaaacccg         40

<210> SEQ ID NO 49
<211> LENGTH: 16
<212> TYPE: DNA
<213> ORGANISM: Artificial Sequence
<220> FEATURE:
<223> OTHER INFORMATION: Synthetic

<400> SEQUENCE: 49
tatggcctgg atctgg         16

<210> SEQ ID NO 50
<211> LENGTH: 16
<212> TYPE: DNA
<213> ORGANISM: Artificial Sequence
<220> FEATURE:
<223> OTHER INFORMATION: Synthetic

<400> SEQUENCE: 50
gttggtggtt ccagtg         16

<210> SEQ ID NO 51
<211> LENGTH: 18
<212> TYPE: DNA
<213> ORGANISM: Artificial Sequence
<220> FEATURE:
<223> OTHER INFORMATION: Synthetic

```
<400> SEQUENCE: 51 ccccttgatga ggaggagc                                              18

<210> SEQ ID NO 52
<211> LENGTH: 19
<212> TYPE: DNA
<213> ORGANISM: Artificial Sequence
<220> FEATURE:
<223> OTHER INFORMATION: Synthetic

<400> SEQUENCE: 52
cttaatgatg gcctgctcc                                              19

<210> SEQ ID NO 53
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (5)..(5)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (34)..(34)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (37)..(37)
<223> OTHER INFORMATION:
      6-amino-3-(2'-deoxy)-D-ribofuranosyl)-5-nitro-1H-pyridin-2-one

<400> SEQUENCE: 53
cntgngctca ttcttaatga tggcrctgct cccncang                         38

<210> SEQ ID NO 54
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (22)..(22)
<223> OTHER INFORMATION:
      2-amino-8-(beta-D-2'-deoxyribofuranosyl)-imidazo-[1,2a]-1,3,5-tri
      azin-[8H]-4-one

<400> SEQUENCE: 54
ccgtgagttg gttctccatn tntcagccct cttatccaac                       40

<210> SEQ ID NO 55
<211> LENGTH: 38
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (18)..(18)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (20)..(20)
<223> OTHER INFORMATION:
      2-amino-8-(beta-D-2'-deoxyribofuranosyl)-imidazo-[1,2a]-1,3,5-tri
      azin-[8H]-4-one

<400> SEQUENCE: 55 gcagggctg aattcctntn ttcgatcttg cggacttc                              38

<210> SEQ ID NO 56
<211> LENGTH: 16
<212> TYPE: DNA
<213> ORGANISM: Artificial Sequence
<220> FEATURE:
<223> OTHER INFORMATION: Synthetic

<400> SEQUENCE: 56
gagacccaaa accagc                                                    16

<210> SEQ ID NO 57
<211> LENGTH: 34
<212> TYPE: DNA
<213> ORGANISM: Artificial Sequence
<220> FEATURE:
<223> OTHER INFORMATION: Synthetic

<400> SEQUENCE: 57
cagcaactgt cccaaagcgc cttgaacagg actg                                34

<210> SEQ ID NO 58
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (15)..(15)
<223> OTHER INFORMATION:
      2-amino-8-(beta-D-2'-deoxyribofuranosyl)-imidazo-[1,2a]-1,3,5-tri
      azin-[8H]-4-one
<220> FEATURE:
<221> NAME/KEY: misc_feature
<222> LOCATION: (31)..(31)
<223> OTHER INFORMATION:
      2-amino-8-(beta-D-2'-deoxyribofuranosyl)-imidazo-[1,2a]-1,3,5-tri
      azin-[8H]-4-one

<400> SEQUENCE: 58
tgggtttncg ctcanccatc cgttcagtcc ntcaggtcag gccagcttct gtcatcg        57

<210> SEQ ID NO 59
<211> LENGTH: 40
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (10)..(10)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (26)..(26)
<223> OTHER INFORMATION:
      6-amino-3-(2'-deoxy)-D-ribofuranosyl)-5-nitro-1H-pyridin-2-one
<220> FEATURE:
<221> NAME/KEY: misc_feature
<222> LOCATION: (33)..(33)
<223> OTHER INFORMATION:
      6-amino-3-(2'-deoxy)-D-ribofuranosyl)-5-nitro-1H-pyridin-2-one

<400> SEQUENCE: 59
ctgacctgan ggactgaacg gatggntgag cgnaaaccca                    40

<210> SEQ ID NO 60
<211> LENGTH: 17
<212> TYPE: DNA
<213> ORGANISM: Artificial Sequence
<220> FEATURE:
<223> OTHER INFORMATION: Synthetic

<400> SEQUENCE: 60
gccagcttct gtcatcg                                             17

<210> SEQ ID NO 61
<211> LENGTH: 16
<212> TYPE: DNA
<213> ORGANISM: Artificial Sequence
<220> FEATURE:
<223> OTHER INFORMATION: Synthetic

<400> SEQUENCE: 61
cttgcggaat ggctgg                                              16

<210> SEQ ID NO 62
<211> LENGTH: 31
<212> TYPE: DNA
<213> ORGANISM: Artificial Sequence
<220> FEATURE:
<223> OTHER INFORMATION: Synthetic

<400> SEQUENCE: 62
ggtggaccat gcccaaagcc ccataggctt c                             31

<210> SEQ ID NO 63
<211> LENGTH: 16
<212> TYPE: DNA
<213> ORGANISM: Artificial Sequence
<220> FEATURE:
<223> OTHER INFORMATION: Synthetic

<400> SEQUENCE: 63
ccttctagct ccctgg                                              16
```

ISOTHERMAL AMPLIFICATION OF OLIGONUCLEOTIDES

CROSS REFERENCE TO RELATED APPLICATIONS

This application claims priority to U.S. provisional patent application No. 62/427,868, filed 30 Nov. 2016, and to co-pending U.S. patent application Ser. No. 14/613,960, filed 4 Feb. 2015, for "Processes for Point of Care Detection of DNA and RNA", which claims priority to the Provisional U.S. Patent Application 61/935,921, filed 5 Feb. 2014.

STATEMENT OF RIGHTS TO INVENTIONS MADE UNDER FEDERALLY-SPONSORED RESEARCH

This invention was made with government support under 1R43AI127037, 1R43GM114967 and 1R21AI128188 awarded by the National Institute of Health, HDTRA1-13-1-0004 awarded by the Defense Threat Reduction Agency, W81XWH-15-C-0007 awarded by the US Army and NNX14AK37G awarded by NASA. The government has certain rights in the invention.

THE NAMES OF PARTIES TO A JOINT RESEARCH AGREEMENT

Not applicable

INCORPORATION BY REFERENCE OF MATERIAL SUBMITTED ON A COMPACT DISK

None

BACKGROUND OF THE INVENTION

1. Field of the Invention

The field of this invention is nucleic acid chemistry, more specifically the field that covers methods for creating a large number of DNA molecules (amplicons) as a consequence of the presence of a target DNA or RNA (collectively xNA) molecule, the "target" or the "analyte". More specifically, the field of the invention concerns amplification procedures that are done without the temperature cycling used in the classical polymerase chain reaction (isothermal amplifications). Most specifically, the field of this invention relates to amplicons derived looped structures. Separately, the feel of this invention comprises nucleic acid analogs that form base pairs independently of the A:T and G:C, nucleotides that are part of an "artificially expanded genetic information system" (AEGIS).

2. Description of the Related Art

Methods that "amplify" nucleic acids (which include both DNA and RNA, as well as various of their analogs, hereinafter xNA) are useful in diagnostics, research, and other biotechnologies. Amplification in this context means a process that yields many product xNA molecules, where the production of those molecules requires a starting xNA sequence, a "target" or an "analyte". Generally, the product xNA molecules (the amplicons) contain within them a segment of DNA whose sequence corresponds to the sequence of a part of the target xNA molecule.

Classically, amplification has been done using the polymerase chain reaction (PCR) [R. K. Saiki, D. H. Gelfand, S. Stoffel, S. J. Scharf. R. Higuchi, G. T. Horn, K. B. Mullis, H. A. Erlich (1988) Primer-directed enzymatic amplification of DNA with a thermostable DNA polymerase. *Science* 239, 487-491]. Here, a "forward primer" that binds by Watson-Crick complementarity to a pre-selected region of a DNA target is annealed to the target to form a duplex. Next, the primer-target complex is incubated with a DNA polymerase and the appropriate 2'-deoxynucleoside triphosphates to yield a Watson-Crick complementary DNA molecule; the target and its complement, as it is formed, are bound in a double stranded double helix. The double strand is then "melted" by heating, typically to temperatures above 75° C., to give the two complementary DNA strands in single stranded form. The mixture is then cooled so that the original target binds to a second forward primer, while its complement binds to a "reverse primer", which is designed to bind to a preselected segment downstream in the product DNA molecule. Then, polymerase extension is repeated, with both primers extended to give full-length products, again as duplexes (now two in number). The results are multiple copies of a segment of the target molecules between the primer binding sites, as well as multiple copies of the complement. In asymmetric PCR, the ratio of these two is different from unity.

Temperature cycling to separate the two strands in PCR is undesirable in many applications, including applications that amplify target DNA at points-of-care. Thus, the art contains many methods that seek amplification methods that do not need temperature cycling, including as "recombinase polymerase amplification" (RPA) [Piepenburg, O., Williams, C. H., Stemple, D. L., Armes, N. A. (2006) DNA Detection using recombination proteins. *PLoS Biol* 4 (7): e204], rolling circle amplification (RCA), NASBA, helicase-dependent amplification (HDA) [Tong, Y., Lemieux, B.; Kong, H. (2011) Multiple strategies to improve sensitivity, speed and robustness of isothermal nucleic acid amplification for rapid pathogen detection. *BMC Biotechnol.* 11 Art. No. 50] [Lemieux, B., Li, Y.; Kong, H. M., Tang, Y. W. (2012) Near instrument-free, simple molecular device for rapid detection of herpes simplex viruses: *Expert Review Molec. Diagnostics* 12, 437-443 DOI: 10.1586/ERM.12.34] and LAMP, among others. These are called "isothermal amplification" methods.

Isothermal amplification methods frequently do not perform well, however. In many cases, the extent of amplification appears to depend on the specific sequence being amplified or (perhaps) the sequence of probes and/or primers used in the amplification. In some cases, the amplification fails entirely. In many cases, extra "spurious" products are observed in addition to the target amplicon. Spurious products are especially often seen when Isothermal amplification is attempted for more than one target nucleic acid in a single sample ("multiplexing).

Essentially no theory explains variable results, although speculation can be found in the public and private art, sometimes informal, and sometimes contradictory. Without being exhaustive, speculative suggestions include the possibility that at low temperatures, non-Watson Crick interactions might cause some of the DNA molecules involved (primer, probe, or analyte) to fold in a way that defeats the amplification process. Others have suggested that high temperatures must be regularly traversed to avoid an (often unknown) intra- or intermolecular interaction from capturing the system as an artifact. Primer-primer interactions have been invoked to explain failure of various isothermal amplification systems, especially when is multiplexing is attempted.

One isothermal amplification method is called "loop-mediated isothermal amplification" (LAMP) [Kubota et al. (2013) Patent Application Publication (10) Pub. No.: US 2013/0171643 A1 Kubota et al. (43) Pub. Date: Jul. 4, 2013 (54) *Sequence Specific Real-Time Monitoring Of Loop-Mediated Isothermal Amplification* (LAMP)]. The LAMP process comprises a reaction involving one or more LAMP primers that bind in a Watson-Crick sense to the target xNA. As illustrated in FIG. 1, LAMP may employ six primers that bind by Watson-Crick complementarity to eight distinct regions within the target analyte. The primers for LAMP are designated as internal primers (FIP and BIP), outer primers (F3 and B3), and loop primers (LB and LF).

LAMP is initiated by adding internal primers (FIP or BIP) that annealed by Watson-Crick complementarity to regions (F2c or B2c) within the target xNA analyte. The outer primer (F3 or B3) then hybridizes to its priming site (F3c or B3c) on the target xNA and initiates the formation of self-hybridizing loop structures by strand invasion of the DNA sequences already extended from the internal primers (FIP and BIP). The resulting dumbbell structure then becomes a seed for exponential LAMP amplification by a strand displacing polymerase.

The synthesis of product molecules process is further accelerated by the loop primers (LF and LB), which are designed to hybridize in oligonucleotide segments between F1c and F2; these are called B1c and B2, respectively, in FIG. 1.

LAMP reactions are generally run under isothermal conditions. Temperatures are commonly fixed at a value between 60° C. and 70° C., sometimes marginally lower, sometimes marginally higher. The amplicons are concatemers of the region in the target that is targeted, and may fold to form "cauliflower-like structures" with multiple loops. The dumbbell structures then are seeds for further amplification.

One of the challenges of the LAMP process is the visualization of the products that are formed. Classically, this has been done by gel electrophoresis to separate the products from the primers based on their longer length. The products form a ladder characteristic of multiple concatemers of different lengths. This is a disadvantage because it does not allow continuous monitoring of the amplification. As another disadvantage, as LAMP produces multiple products, amplicons are spread over the length of a size-resolving gel, lowering signal relative to noise.

In real-time analysis, the creation of LAMP products may be monitored by adding intercalating dyes to the mixture, such as SYBR Green® or EvaGreen®. When double stranded DNA is formed, these dyes bind and, once bound, fluoresce. However, these dyes may inhibit LAMP. Further, this mechanism does not allow the sequence of the DNA product to be confirmed. Thus, the formation of any double stranded products, even those unrelated to the target, can give a false positive signal, in another monitoring process, the progress of LAMP may be followed by measuring the turbidity in reaction mixture arising from precipitating magnesium pyrophosphate, a by-product of LAMP reaction. This method also suffers from a lack of sequence specificity, and therefore susceptible to creating false positives.

Alternative approaches for detecting the products of LAMP-type amplification include the use of molecular beacons [Yaren, O., Bradley, K. M., Moussatche, P., Hoshika, S., Yang, Z., Zhu, S., Karst, S. M., Benner, S. A. (2016) A norovirus detection architecture based on isothermal amplification and expanded genetic systems. *J. Virol. Methods* 237, 64-71], which is incorporated herein in its entirely by reference. Here, a molecular beacon comprises a Watson-Crick self-complementary stem and loop structure that is conjugated to a fluorescent molecule at one end and a quencher molecule at the opposite end. The loop sequence is Watson-Crick complementary to an analyte. In the absence of the analyte, no fluorescence is seen, as the fluorophore and the quencher remain in close proximity. When the loop region hybridizes to the target, however, the quencher and fluorophore are separated from each other, and the beacon emits light via fluorescent emission. However, the use of molecular beacons for real-time monitoring LAMP can be difficult, since stem structure may not be stable at the temperature where LAMP is run. Nevertheless, it may be a useful technique for end-point detection of LAMP amplicons.

An alternative way of visualizing the products uses an "assimilating probe" (FIG. 2) [Kubota, K., Jenkins, D. M., Alvarez, A. M., Su, W. W. (2011) Fret-based assimilating probe for sequence-specific real-time monitoring of loop-mediated isothermal amplification (LAMP). *Biol. Eng. Trans.* 4, 81-100], This adds an additional component of the LAMP reaction mixture. The assimilating probe comprises two DNA strands that hybridize over part of their segment by Watson-Crick complementarity. The first oligonucleotide strand has a fluorescence quenching moiety covalently attached at its 3' end; the second DNA strand of the assimilating probe has a fluorophore covalently attached at its 5'-end. When the two strands are hybridized, the quencher and fluorophore are brought into close proximity, and no fluorescence is seen.

To work, this "assimilating probe" must also have a single stranded region attached to the fluorescently tagged oligonucleotide. This is a priming sequence, and is complementary to a selected segment of the target analyte xNA. The second oligonucleotide strand and the first oligonucleotide strand added to the LAMP reaction are preferably in a ratio of 1:1, although Kubota teach that the ratio in the mixture may be less than 1:1. The art teaches a preferred concentration of the assimilating probes between about 0 μM to about 1 μM.

In LAMP, the priming region of the fluorescently tagged oligonucleotide is extended by a strand-displacing DNA polymerase or reverse transcriptase, with the target analyte xNA being used as a template for the extension. During the LAMP, the primer extension from reverse primers then reads through the primer on the fluorescently tagged oligonucleotide, and then the segment of DNA from the fluorescently lagged oligonucleotide itself, displacing the oligonucleotide that bears the quencher. This separates the florescent species from the quenching species, allowing the fluorescence to be observed and measured from the fluorescently tagged oligonucleotide that has been "assimilated" into the LAMP products.

The process taught by Kubota (2011) for visualizing the products of LAMP suffers from various limitations. First, the LAMP amplification product mixture is what becomes fluorescent. As noted, LAMP does not produce a single product. Rather, it produces a series of product concatemers. This means that the fluorescence is not present in a single molecule that can be captured and observed directly, but rather is distributed among multiple molecules that behave differently, not only on gel electrophoresis, but also by any other separation method.

Further, as taught in Kubota (2011), the two strands in the assimilating probe are held together by Watson-Crick pairing between standard nucleotides. As natural biological samples contain many xNA molecules built from natural nucleotides, these can invade the duplex of the assimilating probe, separate fluorophore and quencher even in the absence of LAMP, creating false positives.

Further, especially when LAMP is multiplexed, the multiple strands of nucleic acid that are added can interact with each other in the presence of polymerases to form undesired products, including primer dimers. These can consume LAMP resources unproductively.

A displaceable architecture that releases a fluorescently tagged species was reported for primers that carried a quencher by Tanner et al. [Tanner. N. A., Zhang Y Fau-Evans, T. C., Jr. and Evans, T. C., Jr. (2012) Simultaneous multiple target detection in real-time loop-mediated isothermal amplification. *BioTechniques* 53, 81-89]. However, these prime internally to the loop, regions FIP and BIP (FIG. 3). Tanner does not teach a process where a fluorophore-releasing probe primes by Watson-Crick complementarity into the loop regions.

Further, neither Tanner (2012) nor Kubota (2012) teach the use of nonstandard nucleotides in the tag regions that hold together the fluorescently labeled oligonucleotide and the quencher oligonucleotide. Here, "nonstandard nucleotides refers to nucleotides built from an artificially expanded genetic information system" (AEGIS) (FIG. 5). AEGIS components have nucleobase analogs with their hydrogen bonding groups are shuffled. This creates new orthogonally binding nucleobase pairs, which cannot hybridize to any natural nucleotide present in any biological sample. Neither Tanner (2012) nor Kubota (2011) teach the use of nonstandard nucleotides in the regions of the primers that bind to the targets or any of the product loop regions.

Finally, neither Tanner (2012) nor Kubota (2012) teach the use of nonstandard nucleotides in the primer regions made from self-avoiding molecular recognition systems (FIG. 6) [Hoshika, S., Leal, N., Chen, F., Benner, S. A. (2010) Artificial genetic systems. Self-avoiding DNA in PCR and multiplexed PCR. *Angew. Chem. Int. Edit.* 49, 5554-5557.]. These prevent primers, present in many types in a standard LAMP architecture, and present in multiplicatively higher numbers in multiplexed detection systems, from interacting with each other.

BRIEF SUMMARY OF THE INVENTION

The instant invention changes the architecture of the process placing the fluorescent species on the displaced oligonucleotide, and the quencher on the priming oligonucleotide, and the primer on the displaceable probe priming on the loop region of an amplifiable structure, rather than on the target analyte itself. This allows the fluorescent species to be a single molecule whose sequence is unrelated to the sequence of the target analyte, and to be released only after the amplification fully starts. This, in turn allows it to be captured, even while the amplification is occurring. This signal sequence is also not spread over many amplicons.

Further in the instant invention, the two components of the reverse displaceable probe hybridize via pairing with nonstandard nucleotides AEGIS (FIG. 5). The advantages of this are several. AEGIS:AEGIS pairing prevents invasion of the displaceable probe by natural nucleic acids, preventing false positives in complex biological mixtures. Further, this allows the displaced fluorescent probe to be captured in real time, even as the amplification is taking place Further in the instant invention, self-avoiding molecular recognition nucleotides may be placed in the priming oligonucleotides (FIG. 6). This prevents the primers from interacting with each other to produce artifacts and wasting amplification resources.

Further in the instant invention, the isothermal amplification can be initiated by a target oligonucleotide that is adsorbed on a solid phase containing quaternary ammonium groups.

U.S. provisional patent application No. 62/427,868, filed 30 Nov. 2016, and to co-pending U.S. patent application Ser. No. 14/613,960, filed 4 Feb. 2015, are incorporated herein in their entirety by reference. Also incorporated herein in their entirety by reference are;

Yaren, O., Bradley, K. M., Moussatche, P., Hoshika, S., Shu, Z., Karst, S. M., Benner, S. A. (2016) A norovirus detection architecture based on isothermal amplification and expanded genetic systems. *J. Virol. Methods* 237, 64-71.

Yaren, O., Glushakova, L. G., Bradley, K. M., Hoshika, S., Benner, S. A. (2016) Standard and AEGIS nicking molecular beacons detect amplicons from the Middle East Respiratory Syndrome coronavirus *J. Virol Methods* 236, 54-61.

Yaren, O., Alto, B. W., Bradley, K. M., Yang, Z., Benner, S. A. (2017) Point of sampling detection of Zika virus within a multiplexed kit capable of detecting dengue and chikungunya. *BMC Infect. Diseases* 17.1, 293

BRIEF DESCRIPTION OF THE DRAWINGS

FIG. 1. The LAMP process adapted from (Nagamine, K., Base, T. and Notomi, T., 2002. Accelerated reaction by loop-mediated isothermal amplification using loop primers. Mol. Cell. Probes, 16, 223-229), which synthesizes multiple concatamers of a nucleic acid, by:

(A) providing a template that has six regions, in the following order from the 3'-end to the 5'-end, termed F3c, F2c, F1c, B1, B2, and B3, (B) providing an external primer, termed F3, that is substantially Watson-Crick complementary to F3c, and (C) providing a first internal primer that has two regions, one F1c towards its 5'-end and the other F2 towards its 3'-end, where the two regions are joined by a linking oligonucleotide, and where F1c is substantially Watson-Crick complementary to F1 and F2 is substantially Watson-Crick complementary to F2c.

Polymerase-catalyzed extension of the first internal primer generates a first copy that comprises F1c, F2, F1, B1c, B2c, and B3c in the 5- to 3' direction, wherein F1c is substantially Watson-Crick complementary to F1, F2 is substantially Watson-Crick complementary to F2c, F1 is substantially Watson-Crick complementary to F1c, B1c is substantially Watson-Crick complementary to B1, B2c is substantially Watson-Crick complementary to B2, and B3c is substantially Watson-Crick complementary to B3. Then, through (D) providing a second external primer, termed B3, which is substantially Watson-Crick complementary to B3c and (E) providing a second internal primer that has two regions, one B1c towards its 5'-end and the other B2 towards its 3'-end, where the two regions are joined by a linking oligonucleotide, and where B1c is substantially Watson-Crick complementary to B1 and B2 is substantially Watson-Crick complementary to B2c.

Polymerase-catalyzed extension of the second internal primer generates a second copy that comprises B1c, B2, B1, F1c, F2c, and F1 in the 5'- to 3' direction, this second copy can form a structure having two loops.

Figure 2:
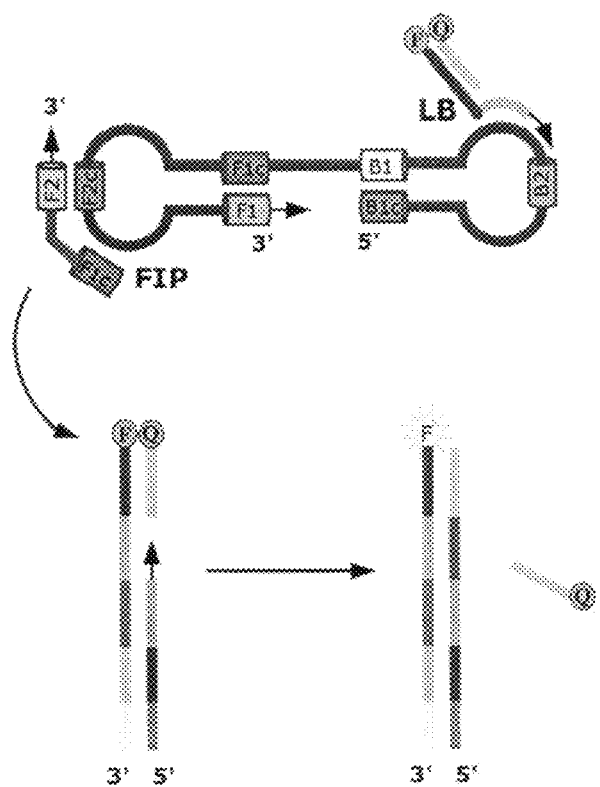

FIG. 2. The LAMP process with assimilating probes as disclosed in Kubota [Kubota, K., Jenkins, D. M., Alvarez, A. M. and Su, W. W., 2011. Fret-based assimilating probe for sequence-specific real-time monitoring of loop-mediated isothermal amplification (LAMP). Biol. Eng. Trans. 4, 81-100]. Here, a primer complementary to the loop carries a fluorescently labeled moiety, which allows the concatamer to be fluorescent.

Figure 3:
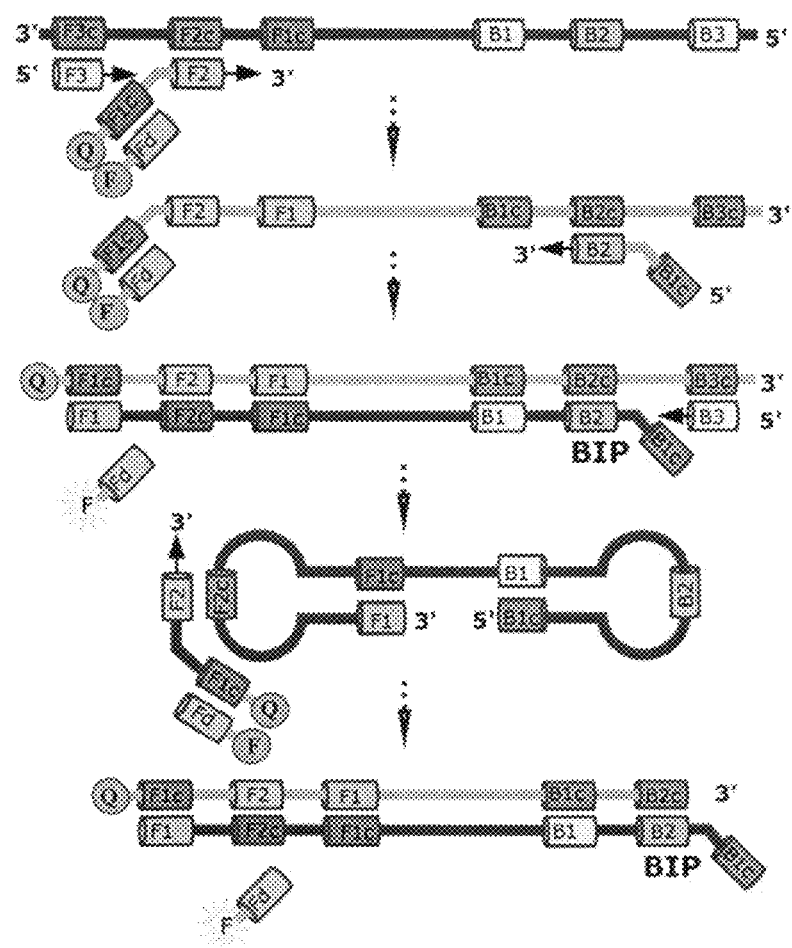

FIG. 3. The LAMP process with reverse displaceable detection architecture as disclosed by Tanner [Tanner, N. A., Zhang Y Fau-Evans, T. C., Jr. and Evans, T. C., Jr., 2012. Simultaneous multiple target detection in real-time loop-mediated isothermal amplification. BioTechniques 53, 81-89]. Tanner places fluorescent tags on the internal primer. However, this is believed to slow down the amplification.

Figure 4:
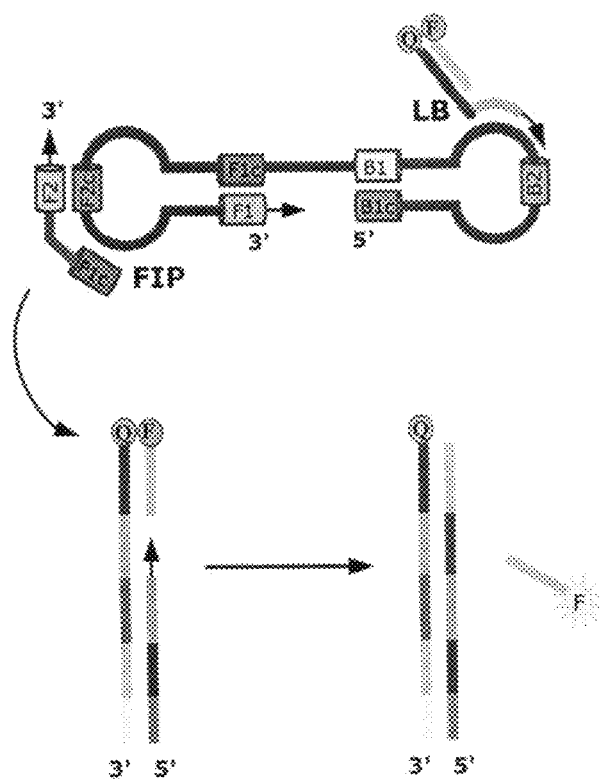

FIG. 4. The process for creating detectable signal in the process of instant invention as disclosed here adds a tagged primer that is a DNA molecule comprising two regions, the first tag region carrying a fluorescence quenching moiety at or near its 5'-end and the second tag region substantially Watson-Crick complementary to a region between B1 and B2 or a region between F1 and F2, and a displaceable probe that is a DNA molecule having a fluorescent moiety at or near its 3'-end, said displaceable probe being substantially Watson-Crick complementary to the first tag region. The first key inventive difference is the attachment of the fluorescent moiety to a species that is displaced and potentially captured elsewhere or detection. The concatamer itself does not become fluorescently labeled.

Figure 5:
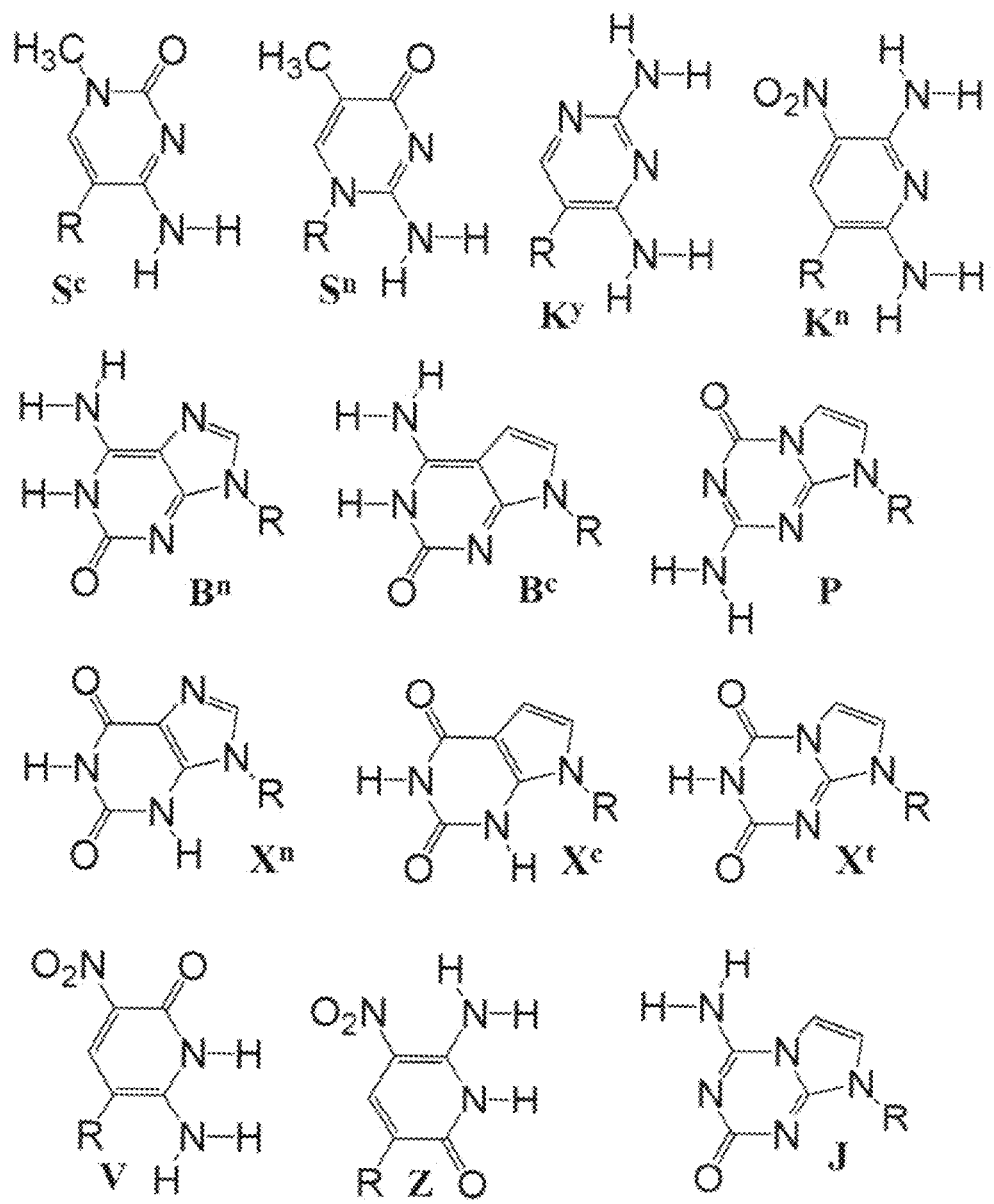

FIG. 5. Components of an artificially expanded genetic information system that may be incorporated into the tags on the reverse displaceable probe pairs.

Figure 6:
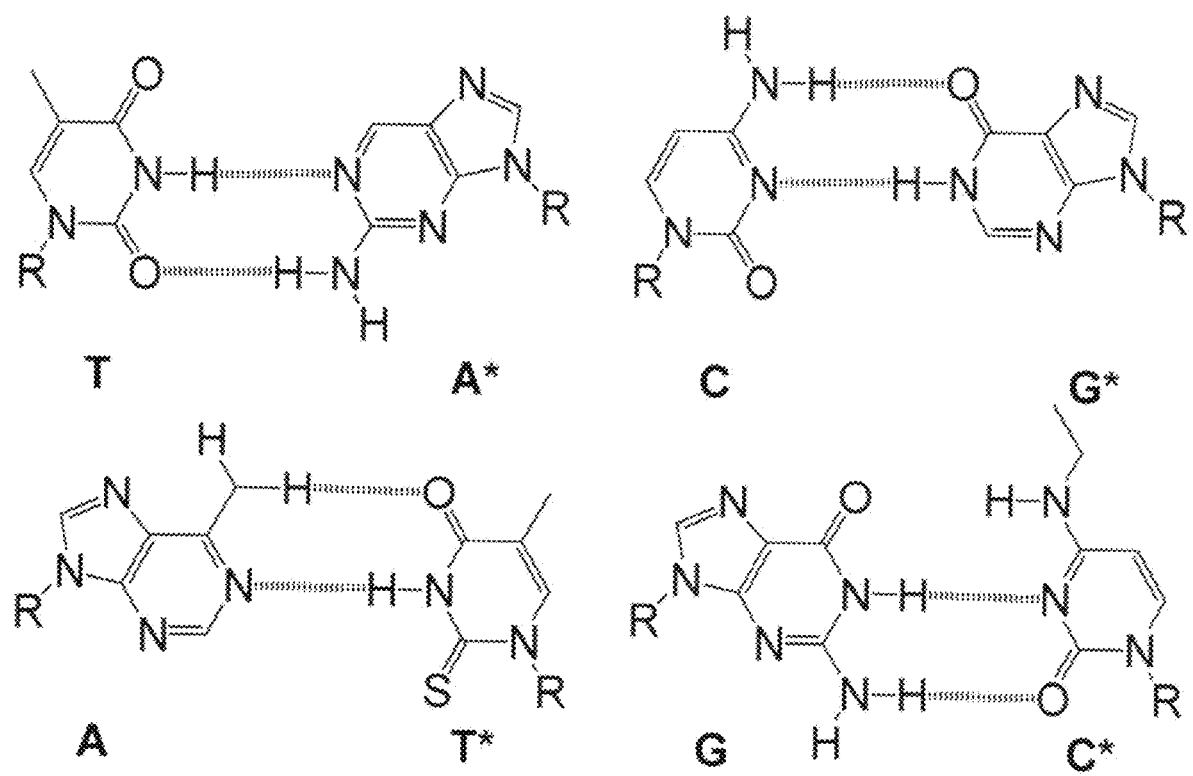

FIG. 6. Self-avoiding molecular recognition nucleotides that may be placed in the priming oligonucleotides.

Figure 7:
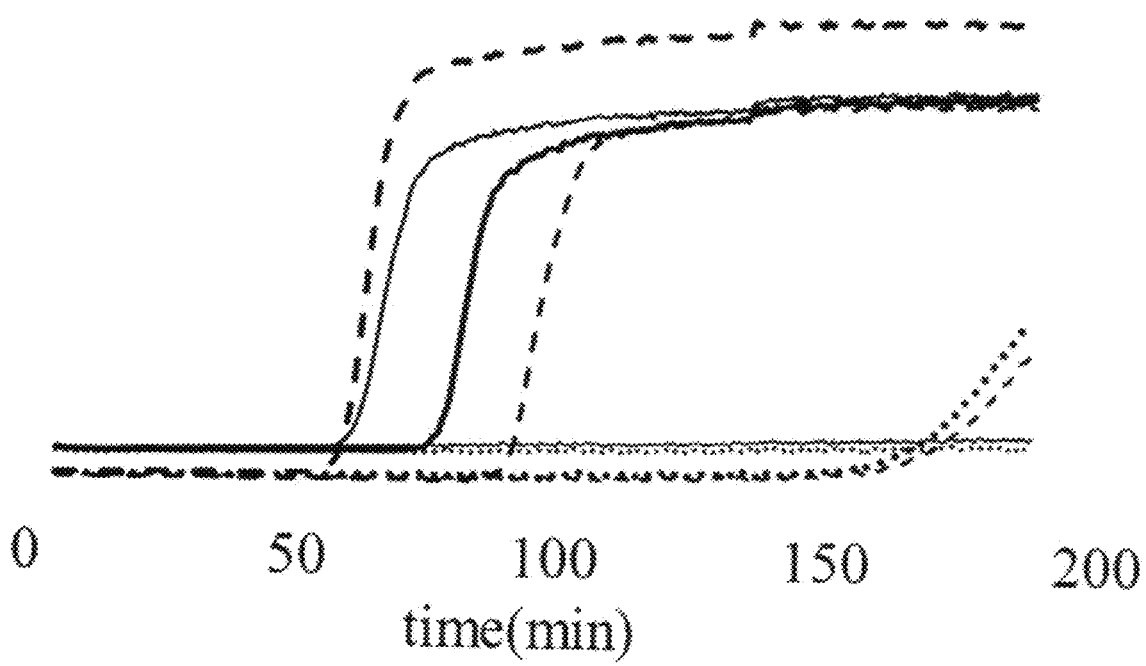

FIG. 7. Data from Example 1. (A) Following fluorescence in real-time showing AEGIS LAMP starting from RNA. Dotted line is the no-target control with AEGIS components. Dotted bold line is the no-target control without AEGIS components. Solid bold is AEGIS with 10 pg of RNA target. Solid not bold is AEGIS with 1 pg of RNA target. Solid light is AEGIS with 0.1 pg of RNA target. Dashed bold is standard DNA without AEGIS with 10 pg of RNA target. Dashed not bold is standard DNA without AEGIS with 1 pg of RNA target. Dashed light is standard DNA without AEGIS with 0.1 pg of RNA target. These results show that this system works with AEGIS components. (B) The temperatures at various times in the incubation (68-60° C.).

Figure 8:
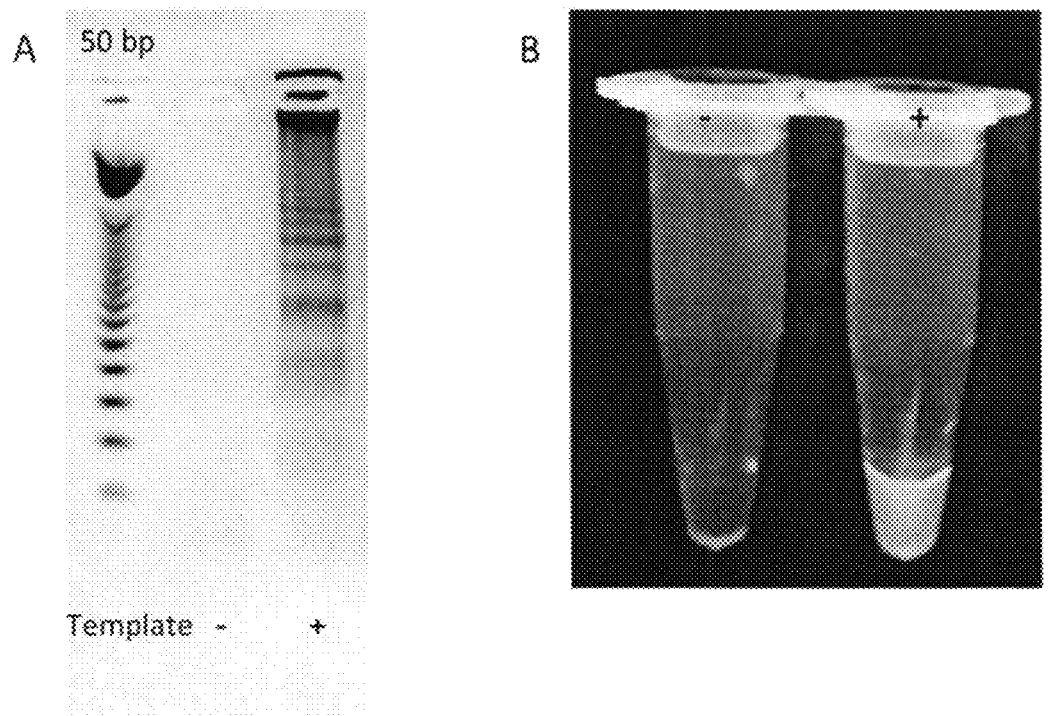
Figure 8:
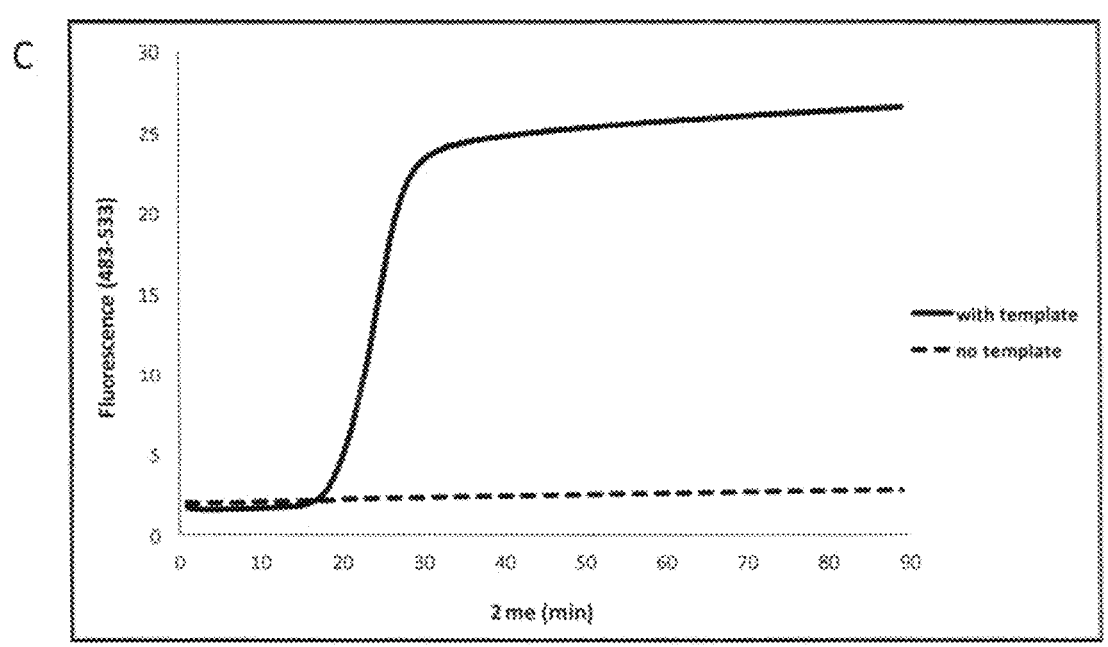

FIG. 8. Results of the process of the instant invention applied to mosquitoes squished on-Q paper, targeting SSU rRNA. (A) Gel electrophoresis of the amplicons in the absence or presence of the target. (B) Fluorescence visualization of the products under LED excitation (470 nm) with orange filter. (C) Real-time monitoring of the instant invention process using reverse displaceable probes.

Figure 9:
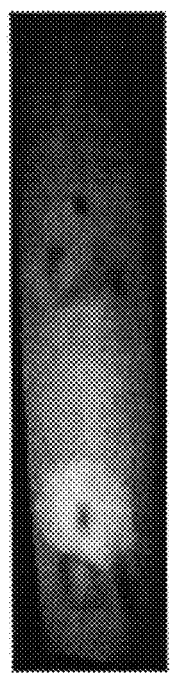

FIG. 9. Results of the capture of displaced probes on a solid support. Complimentary oligonucleotide was manually printed on chemically functional solid phase support. Fluorescently labeled displaced probe detecting ribosomal RNA of Ae. aegypti was hybridize to its complementary probe through capillary transport.

Figure 10:
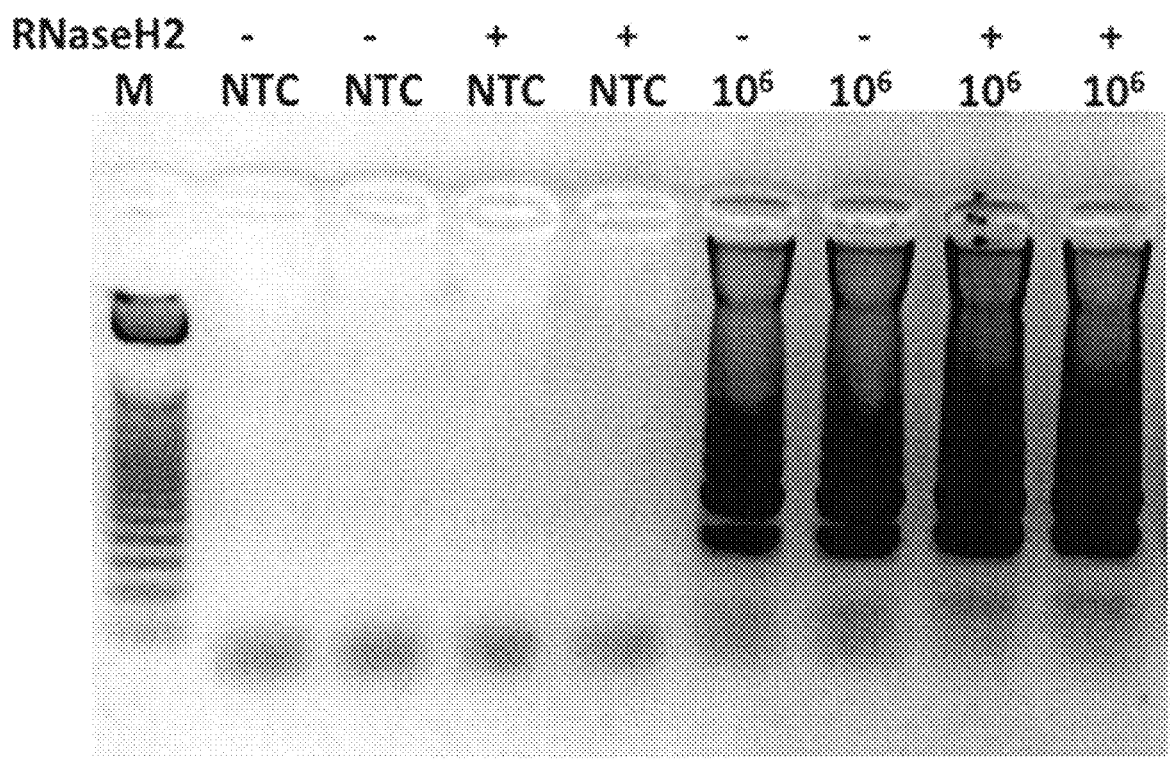

FIG. 10. Gel electrophoresis analysis of the products of Aegis-LAMP from plasmid DNA in the absence (−) or presence (+) of RNase H2, run in duplicate. Plasmid DNA standard ($10^6$ copies) was mixed with LAMP components and incubated at 65° C. for 45 min. Samples (5 μL) after isothermal amplification were run on 2.5% TBE agarose gels (M is a 50 bp ladder, NTC is the negative control). Note the "ladder" of products, and notice that the primers disappear in the presence of RNase H2 (last two lanes).

Figure 11:
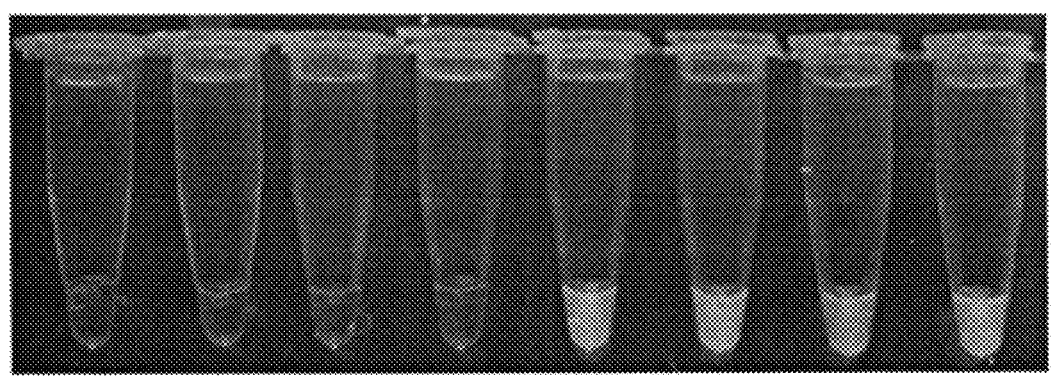

FIG. 11. Beacon analysis of the same products by signals arising from AEGIS RNase H-nicking beacons, giving eye-visible signals captured by cell phone camera (fluorescein, DABCYL quencher, 475 nm LED illumination). Plasmid DNA standard ($10^6$ copies) was mixed with LAMP components and incubated at 65° C. for 45 min. (or visualized by AEGIS RNase H2 nicking beacon that is present during the LAMP. Notice that the primers disappear in the presence of RNase H2.

Figure 12:
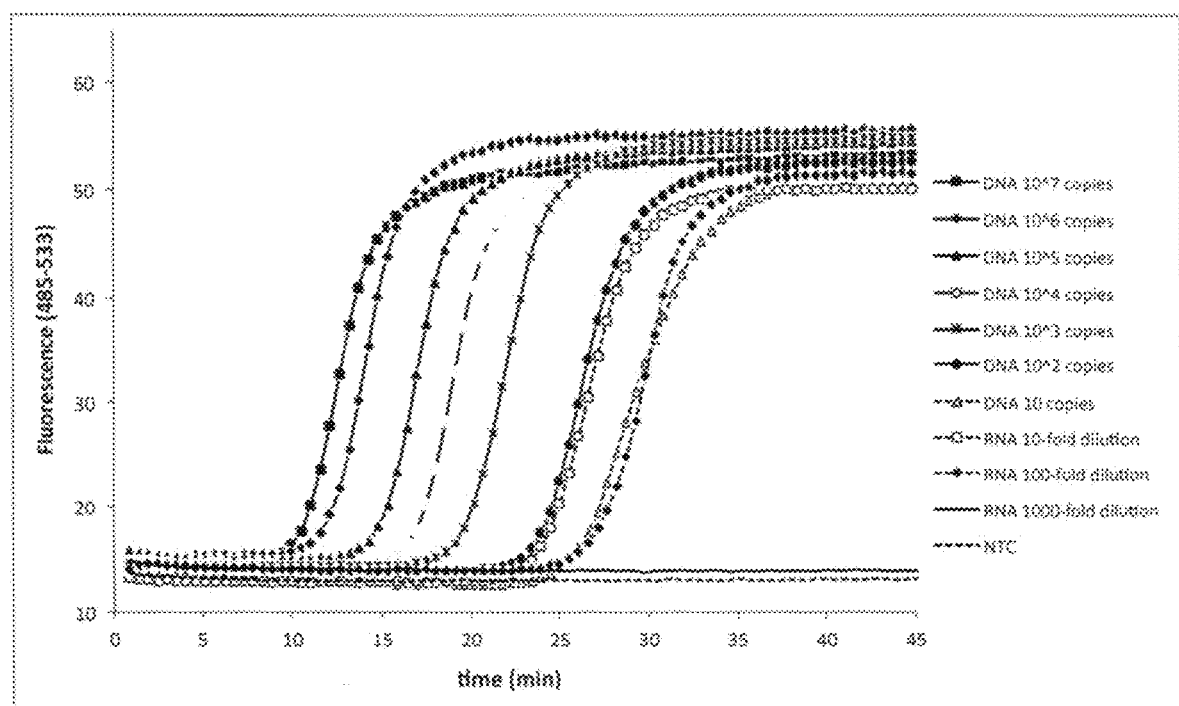

FIG. 12. From Example 3, estimating "effective viral load" in stool samples by real time reverse transcriptase loop-mediated isothermal amplification (RT-LAMP). This was done from plasmid DNA containing norovirus sequences (top lines) as well as RNA isolated from stool using Trizol. For plasmid DNA standard, serial dilutions yielded samples (25 μL) containing $10^7$ to $10^1$ copies per μL. For extracted RNA, serial dilutions up to 1000 fold generated samples whose amounts of virus were calculated by comparison with the DNA-determined "standard curve", under the assumption that LAMP and RT-LAMP had identical efficiencies. The LAMPs had primers Ae-FIP and Ae-BIP (1.6 μM each), F3 and B3 (0.2 μM each), and LB and LF (0.4 μM each), dNTPs (1.4 mM each), MgSO$_4$ (4 mM), dPTP (0.5 mM), dZTP (0.05 mM), Bst 2.0 WarmStart DNA polymerase (8 Units) and 0.4× EvaGreen stain (to allow real time detection) in 1× LAMP buffer with WarmStart RTx Reverse transcriptase (NEB 7.5 U) included for RNA samples. Mixtures were incubated (65° C., Light Cycler 480, Roche) with continuous fluorescence monitoring. Reactions were complete in about 30 min. Adapted from [Yaren, O., Bradley, K. M., Moussatche, P., Hoshika, S., Shu, Z., Karst, S. M., Benner, S. A. (2016) A norovirus detection architecture based on isothermal amplification and expanded genetic systems. J. Virol Methods 237, 64-71.], which is incorporated herein in its entirety by reference.

Figure 13:
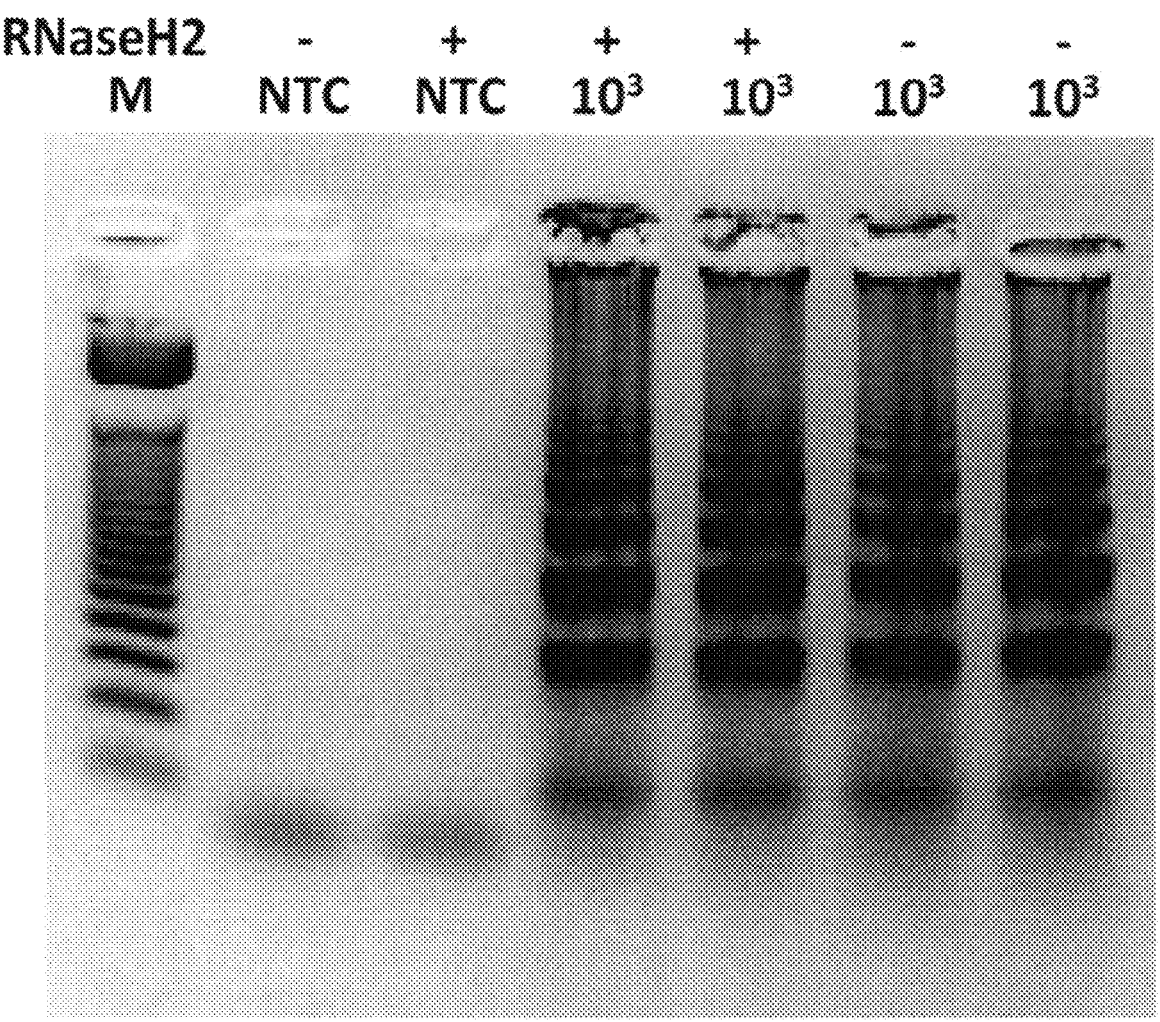

FIG. 13. Analysis of AEGIS-RT-LAMP with signaling from AEGIS RNase H-nicking beacons to give eye-visible signals captured by cell phone camera (475 nm LED illumination). Trizol extracted RNA ($10^3$ copies) was mixed with LAMP components in the absence/presence of RNase H2 and incubated at 65° C. for 45 min. (A) Samples (5 μL) were run on 2.5% TBE agarose gels (M as 50 bp ladder, NTC as no template control).

Figure 14:
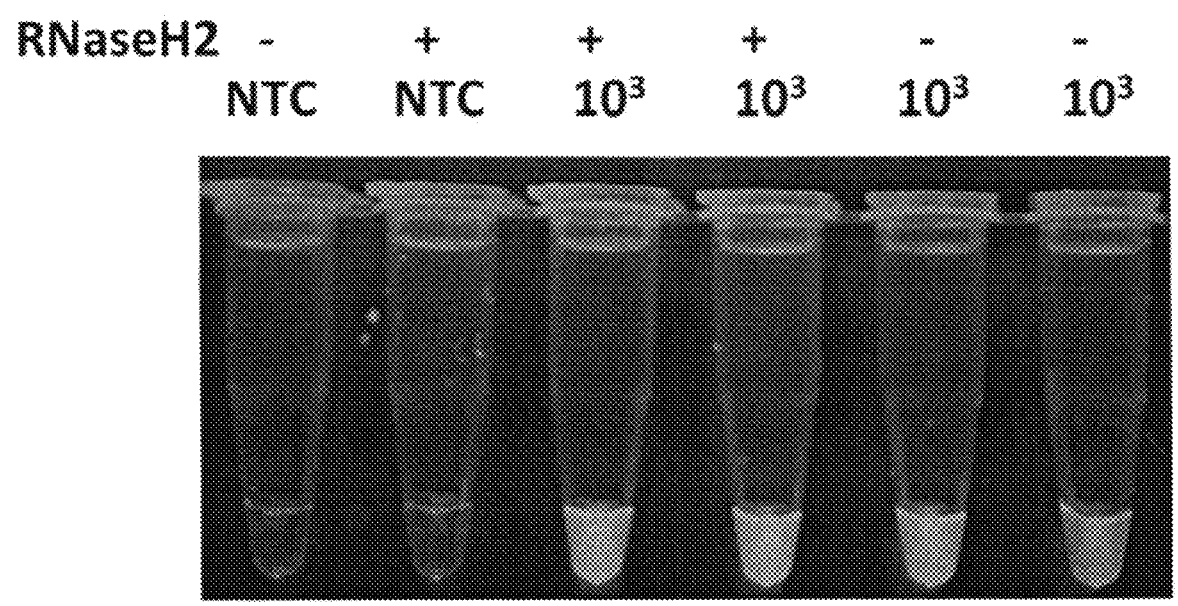

FIG. 14. As in FIG. 13, but visualized by AEGIS RNase H nicking beacon that is present throughout the LAMP. Samples were run in duplicates.

Figure 15:
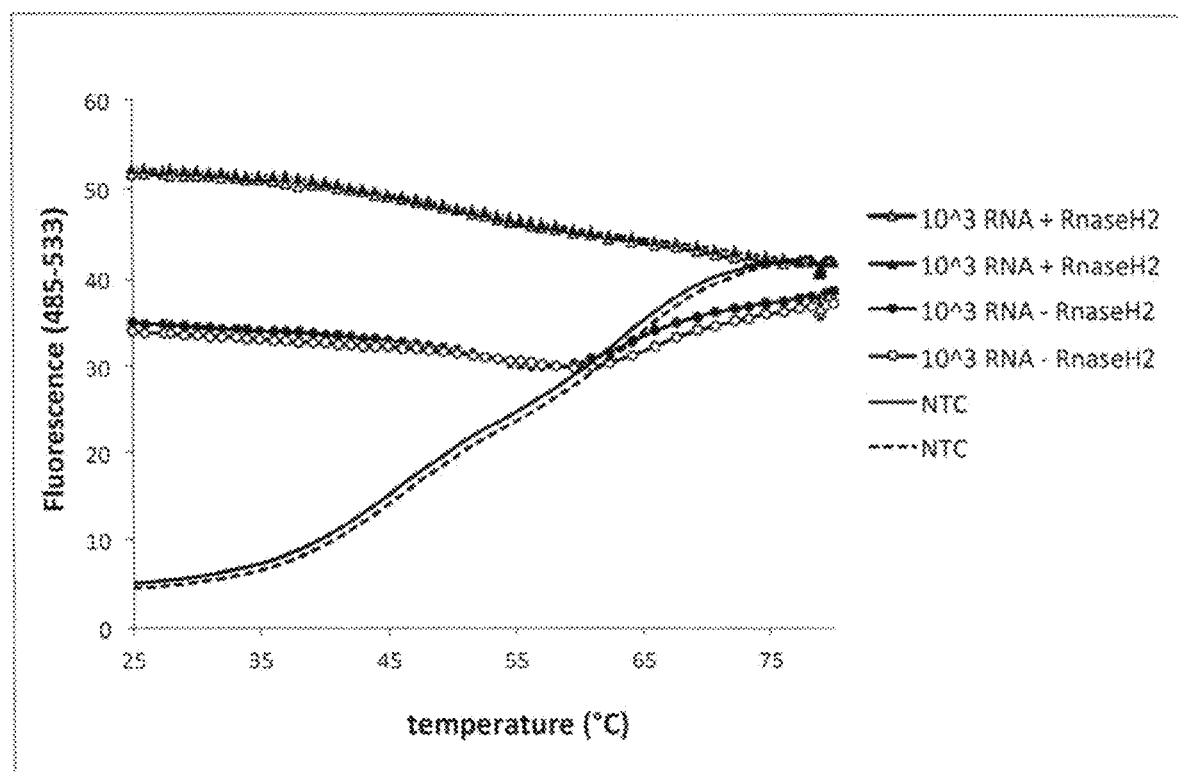

FIG. 15. As in FIGS. 13 and 14, thermal profiles of AEGIS MBs were recorded with LAMP amplicons in the absence/presence of RNase H2. In the negative controls lacking target, the beacons thermally open at 65° C. but the fluorescence diminishes when the temperature is lowered and the beacon hairpin closes. Upon cooling in the absence of RNase H2, the fluorescence remains only for beacons that, at the time of observation, are bound to an amplicon. However, with RNase H2, beacons that have ever been bound to an amplicon continue to glow, as well as those that are bound (at the time of observation) to an amplicon. Quantitatively, this is shown by the duplicates generated with RNase H2 (light blue and magenta) having ~2× more fluorescence than the duplicates generated without RNase H2 (orange and green). Qualitatively, this can even be observed by eye in the tubes.

Figure 16:
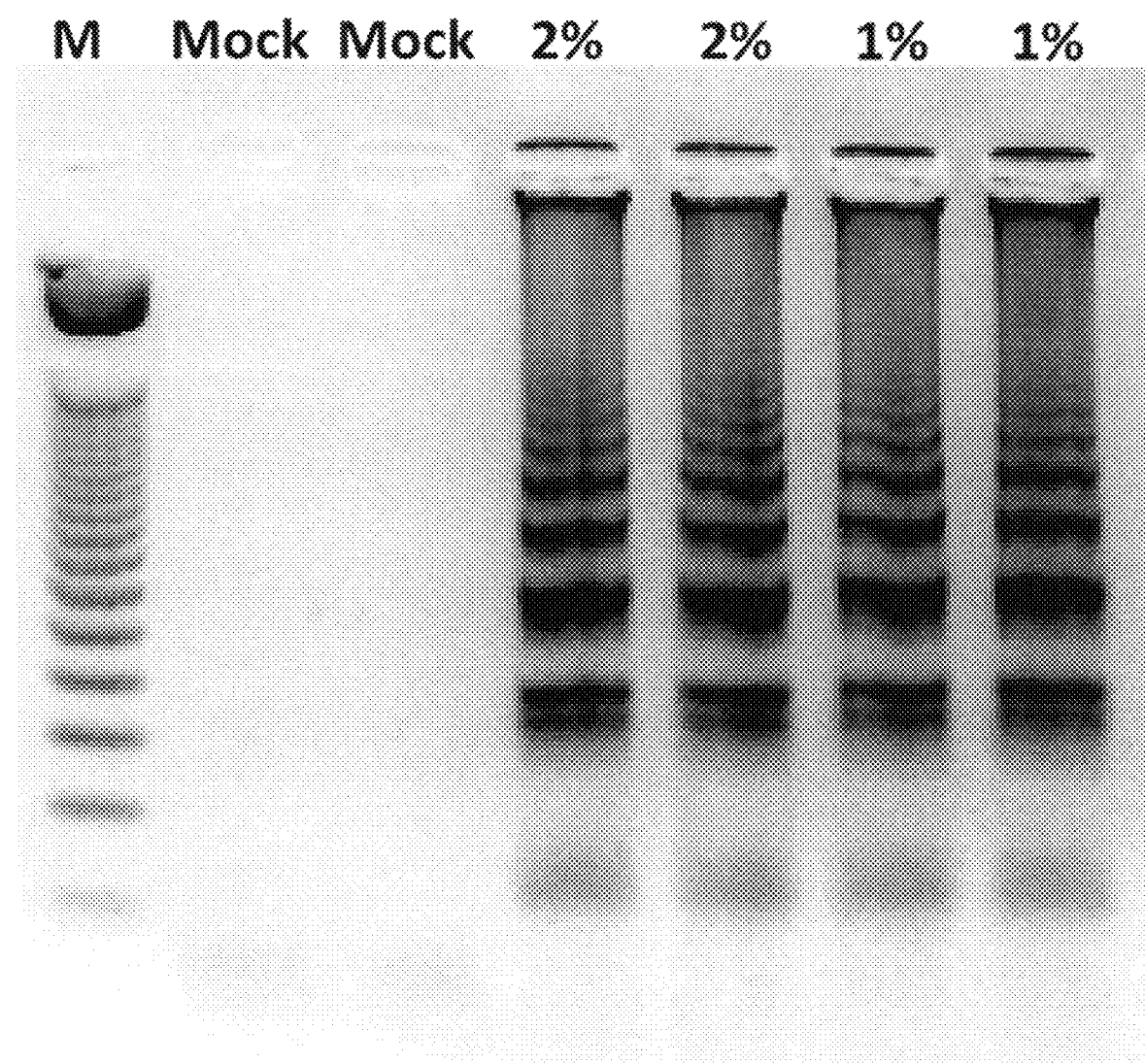

FIG. 16. AEGIS RT-LAMP with RNase H2 generated signals by gel. Specifically, stool infected with MNV-1 (50 mg, ~50,000 virions) was resuspended in aqueous Tris-HCl (10 mM, pH 7.9, 2% and 1% w/v). Aliquots (5 µL) were treated with ammonium hydroxide (30 mM $NH_4OH$, 20 mM DTT, pH 11.1). The mixture was moved to 65° C. and, after 5 min, RT-LAMP components were added. LAMP amplification was stopped at 45 min. Samples were then run on 2.5% TBE agarose gels (M as 50 bp ladders, mock as mock-inoculated samples). Samples were prepared with simple dilution, without removing inhibitors.

Figure 17:
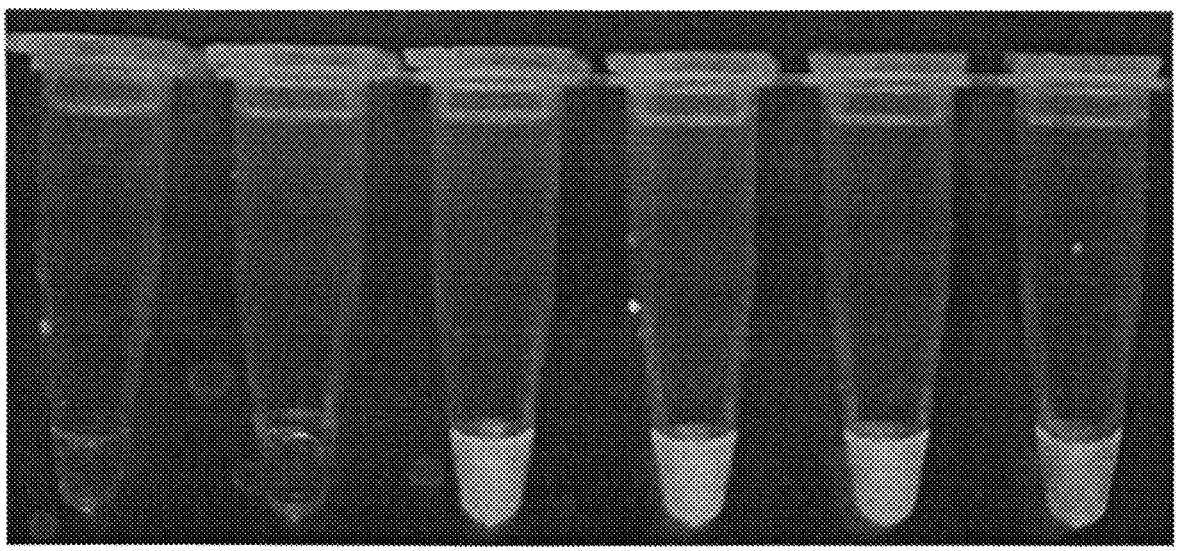

FIG. 17. As in FIG. 16, but visualized by AEGIS RNase H2 cleavable beacon present throughout the LAMP.

Figure 18:
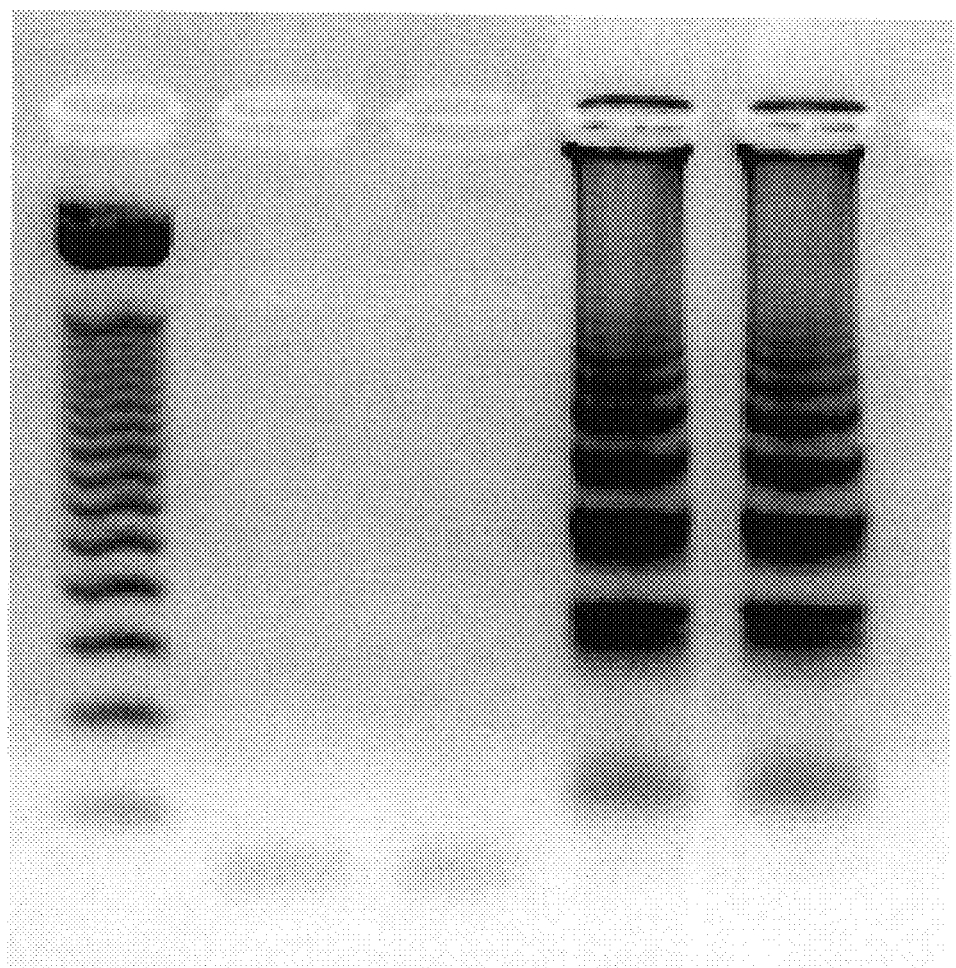

FIG. 18. As with FIG. 16, but with a step to remove inhibitors by size-exclusion centrifugation (with 100 kDa cut-off limit). Comparable results showed no evidence of LAMP inhibitors in these amounts of stool.

Figure 19:
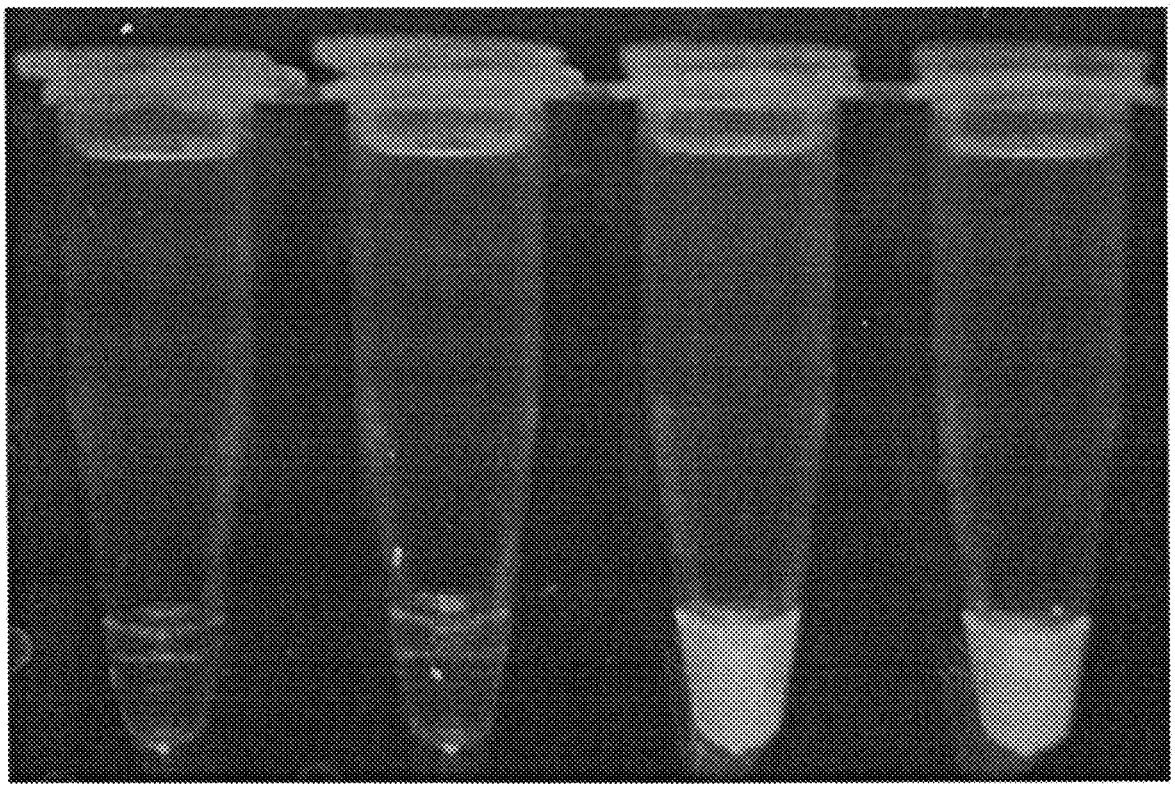

FIG. 19. As with FIG. 17, but with a step to remove inhibitors by size-exclusion centrifugation (with 100 kDa cut-off limit). Comparable results showed no evidence of LAMP inhibitors in these amounts of stool.

Figure 20:
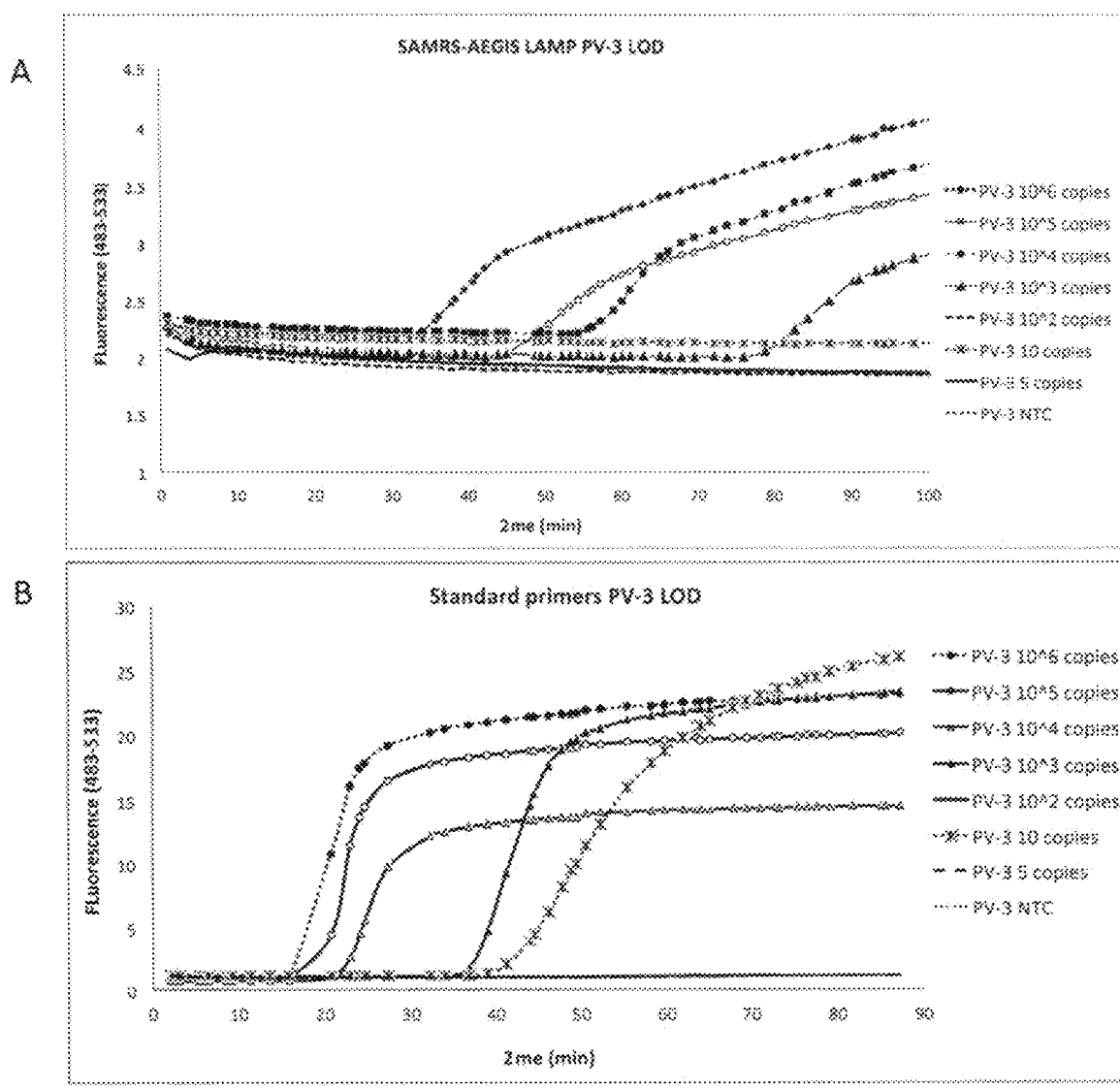

FIG. 20. Serially diluted DNA templates targeting Powassan virus were run in real time LAMP for determination of limit of detection. (A) 1000 copies of target were detected in 80 min with self-avoiding nucleotides as specified in the primers, and AEGIS on the displaced probe. (B) This can be compared with standard primers, where 1000 copies were detected in 50 min.

DETAILED DESCRIPTION OF THE INVENTION

Embodiments of the instant invention present gene-based diagnostics capable of rapidly detecting pathogens. Examples may include, but are not limited to, both DNA and target analytes, with the presently preferred analytes being the RNA molecules from the RNA viruses known in the art as Zika, Dengue, and Chikungunya.

The core of the instant invention is illustrated in FIG. 4. Here, after the initial loop is formed, the amplification process is carried by a primer (LB) that comprises two components: (a) a priming segment that is complementary to a single-stranded region of the loop, and (b) a tag segment appended to the 5'-end of the priming segment that carries a fluorescence quencher at its 5'-end; the tag sequence is preferably not complementary to any xNA in the system, neither in the target analyte itself or any other nucleic acid that might be present adventitiously.

The level of invention is use of "reverse displaceable probes", rather than the assimilating probes of Kubota (2011) to generate a sequence. Specifically, the fluorescent species (F, in a circle, FIG. 4) is attached not to the oligonucleotide that serves as a primer in the process that carries forward the amplification after a loop has been formed, but rather on an oligonucleotide that hybridizes to that primer and is displaced in the process that carries the amplification forward. Further, the priming oligonucleotide has a quencher placed so that when the priming oligonucleotide hybridizes to the displaced oligonucleotide, the quencher comes near to the fluorophore attached to the displaced oligonucleotide. Thus, when hybridized, the fluorescence from the fluorophore is quenched, and not observable. However, during the process of instant invention, when the displaceable oligonucleotide is displaced, the fluorophore is separated from the quencher, and its fluorescence can be observed.

To implement this method, the probe and the tag must be substantially Watson-Crick complementary over the segments that form a duplex. The presently preferred embodiment of the instant invention has the duplex being no less than 20 base pairs in length, and not more than 50. Operationally, the duplex is preferably long enough to be stable enough to remain associated at the temperatures where the amplification is run, without dissociation to a level that causes background fluorescence to arise from dissociated strands. Most preferably, the duplex is 35±5 base pairs in length. Further, the presently preferred embodiment has each nucleotide in the probe correctly match, in the Watson-Crick sense, the paired nucleotide in the tag. This means, as is very well known in the art, that A is matched to T, and C is matched to G.

For AEGIS pairs, AEGIS nucleotides in the tag are matched with the AEGIS nucleotide in the probe that presents the complementary hydrogen bonding pattern. For example, AEGIS P pairs with AEGIS Z. The same is presently preferred for non-standard nucleotides that present standard hydrogen bonding pairs; for example, diaminopurine or oxoformycin B is matched with pseudothymidine. These rules are described in [Benner, S. A., Karalkar, N. B., Hoshika, S., Laos, R., Shaw. R. W., Matsuura, M., Fajardo, D., Moussatche, P. (2016) Alternative Watson-Crick synthetic genetic systems. *Synthetic Biology*, Cold Spring Harbor Perspectives in Biology, Cold Spring Harbor Press. PMID: 27663774.], which is incorporated herein in its entirety by reference.

However, an occasional mismatch is possible in the duplex between the tag in the probe, and has occasional advantages in the performance of the system. So long as the number of mismatches does not lower the melting temperature of the duplex to the temperature at which the amplification is run, such substantially complementary duplexes have utility as well. Most preferably, those mismatches do not exceed one in 20 base pairs.

The art contains multiple methods for attaching fluorescent and fluorescence quenching moieties to DNA molecules. Many fluorescent moieties are available in the art, and many quencher moieties are available in the art; DNA molecules carrying many of these can be purchased commercially. As illustrated in our examples, without limitation, the presently preferred fluorescent moieties are FAM, HEX, TET, TAMRA, Cy3, and Cy5. The presently preferred fluorescence quenchers are Black-FQ, DABCYL, TAMRA, and Black Hole Quencher.

To be suitable implementations of the instant invention, the points of attachment of the fluorescent moiety to the tag oligonucleotide and of the fluorescence quenching moiety to the probe must be selected so as to bring the fluorescent moiety and the quenching moiety in proximity in three-dimensional space once the tag and the probe are hybridized in a Watson-Crick sense. Presently preferred is the attachment of the fluorescent moiety at or near the 5'-end of the tag. In this context, at the 5'-end means attachment of the fluorescence moiety by way of a phosphodiester linkage made to the free 5'-hydroxyl group of the 5'-terminal nucleotide. "Near" the 5'-end means most preferably attachment of the fluorescent group to a nucleobase by way of a side chain attached to the 5-position of a pyrimidine nucleoside at or near the 5'-end of the tag.

Likewise, the presently preferred position for attachment of the quenching moiety is at or near the 3'-end of the probe. In this context, "at" the 3'-end means attachment of the fluorescent moiety by way of a phosphodiester linkage made to the free 3'-hydroxyl group of the 3'-terminal nucleotide.

"Near" the 3'-end means attachment of the fluorescent group to a nucleobase by way of a side chain attached to the 5-position of a pyrimidine nucleoside at or near the 3'-end of the tag. Other details of attachment that achieve the goal of bringing the fluorescent moiety and the quenching moiety together in space when the probe and the tagger hybridized are well known in the art.

Further, as a consequence of this inventive architecture, the fluorescently tagged displaceable oligonucleotide is single-stranded, specific molecule, and has a structure that is entirely under the control of the designer. Therefore, should the amplicons be detected by gel electrophoresis, the signal all appears in a sharp single band, not spread across the entire gel. Further, since the priming is on the loop, the signal is created only after the instant invention fully starts. Therefore, it cannot be created by any of a number of artifacts that are common in LAMP.

In complex biological media, of course, it is difficult or impossible to know what other xNA sequences might be present. Therefore, it is difficult to design the tag sequence and the sequence of the displaceable probe. However, because the duplex region holding together the two oligonucleotides of the reverse displaceable probe is independent of the sequence of the target, those sequences can be built from unnatural DNA analogues, including components of a artificially expanded genetic information system (AEGIS, FIG. 5).

AEGIS is described in detail in [Benner, S. A., Karalkar, N. B., Hoshika, S., Laos, R., Shaw. R. W., Matsuura, M., Fajardo, D., Moussatche, P. (2016) Alternative Watson-Crick synthetic genetic systems. *Synthetic Biology*. Cold Spring Harbor Perspectives in Biology, Cold Spring Harbor Press. PMID: 27663774.], which is incorporated herein in its entirety by reference. This publication makes references to procedures for the synthesis of AEGIS-containing oligonucleotides.

In summary, all natural DNA is composed of four nucleotides that pair following two rules of complementarity, size complementarity (big purines pair was small pyrimidines) and hydrogen bonding complementarity (hydrogen bond donors pair with hydrogen bond acceptors). AEGIS increases the number of independent the pairing nucleobase pairs by shuffling the hydrogen bonding groups, while retaining size commentary. AEGIS pairs form orthogonally to natural pairs; that is, a DNA sequence containing AEGIS components cannot pair with any sequence containing just the four natural bases.

Introduction of AEGIS into the tag:probe pair solves the problems outlined above that arise by the invasion of the duplex from adventitious nucleic acids. By placing AEGIS:AEGIS pairs into the tag:probe duplex, the duplex cannot possibly be disrupted by hybridization of either oligonucleotide to any standard DNA or RNA molecule that might be present in a complex biological sample. Watson-Crick pairing within the displaceable probe between nonstandard AEGIS nucleotides prevents invasion of the displaceable probe by natural nucleic acids, and also prevents a certain class of false positives. Further, because the fluorescently labeled AEGIS probe cannot find anything in the amplification mixture, it can diffuse to a complementary AEGIS capture molecule that may for example be localized by covalent immobilization inside of a detection zone. There can be concentrated and read by fluorescence spectroscopy. Alternative tags are also possible, including those that have electrochemical readouts, radiochemical readouts, and chemical reactivity readouts.

To be useful, the AEGIS nucleotides in the tag must be sufficient in number to destabilize any duplex that can be formed with any standard oligonucleotide sufficiently to prevent the tag from hybridizing to any possible standard oligonucleotide at tire temperature at which the amplification is run. Likewise, to be useful, the AEGIS nucleotides placed in the probe must be sufficient in number to destabilize any duplex that can be formed with any standard oligonucleotide sufficiently to prevent the probe from hybridizing to any possible standard oligonucleotide at the temperature at which the amplification is run strand. The number of such mismatches can be determined experimentally by pairing an AEGIS-containing probe or tag to a standard complement candidate so as to pair the AEGIS with its best favorable mismatch (e.g., pairs AEGIS P with standard C, or AEGIS Z with standard G. Rules to guide such experiments are well known in the art [Wang, X., Hoshika, S., Peterson, R. Kim, Benner, S. A., Kahn, J. (2017) Biophysics of artificially expanded genetic information systems. Thermodynamics of DNA duplexes containing matches and mismatches involving 2-amino-3-nitropyridin-6-one (Z) and imidazo[1,2-a]-1,3,5-triazin-4(8H)one (P) *ACS Synth. Biol.* 6, 782-792]. However, the presently preferred embodiments of the instant invention simply have 3 to 5 AEGIS nucleotide pairs in a probe/tag duplex that is most preferably 35±5 nucleotides in length, with the AEGIS nucleotides separated by preferably 3-8 standard nucleotides, most preferably 5. The most presently preferred embodiment has AEGIS P in the tag and AEGIS Z in the probe. The second most preferable is to have AEGIS Z in the tag and AEGIS P.

A priori, it was not clear that any loop-involving architecture would accept AEGIS nucleotides. Accordingly, a key element in creating this invention was the demonstration, shown in Example 1, that certain AEGIS nucleotides were in fact accepted in the innovative loop-involving architecture disclosed here. Many polymerases do not perform well, or do not perform at all, with the amplification architecture of the instant invention. However, those that accept C glycosides have been found to have utility. Thus, are presently preferred polymerase is Bst 2.0 WarmStart® DNA Polymerase. As is obvious to those in the art, the temperature at which the amplification is run must be compatible with the polymerase used. Further, temperatures substantially below 60° C. do not perform well. Accordingly, the presently preferred temperature is between 60 and 70° C., most preferably 65±1° C.

Figure 1:
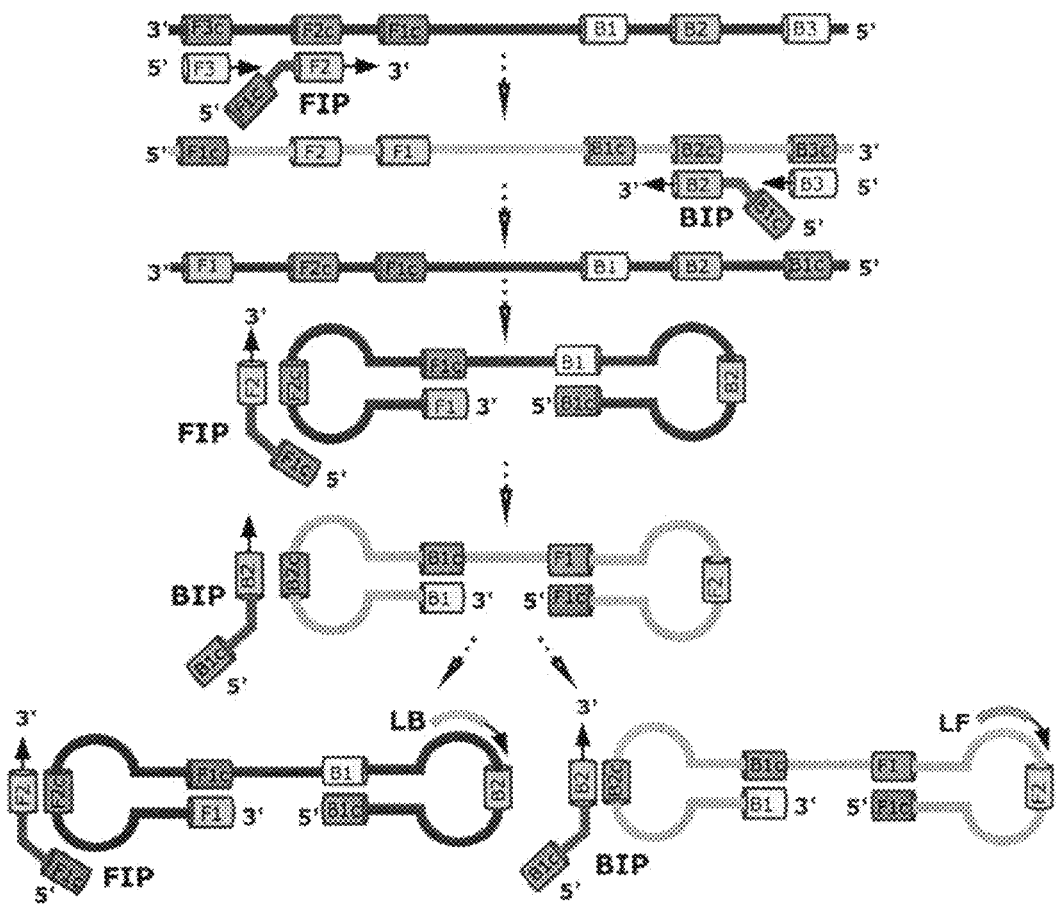

Further utility in the instant invention is gained by multiplexing the system, that is, adding primers and detectors that target many different xNA analytes. Here, the number of single-stranded segments to be added to a mixture can easily become unwieldy (FIG. 1). In particular, in the presence of a polymerase, these can partially hybridized to each other, creating artifacts known as primer dimers, creating background noise and consuming amplification resources.

Therefore, in a third level of invention, self-avoiding nucleotides may be placed in the single stranded oligonucleotides that support this process (FIG. 6). These are described in [Hoshika, S., Leal, N., Chen, K, Benner, S. A. (2010) Artificial genetic systems. Self-avoiding DNA in PCR and multiplexed PCR. *Angew. Chem. Int. Edit.* 49, 5554-5557], which is hereby incorporated in its entirety by reference. These analogues of the standard four nucleobases prevent single-stranded DNA molecules containing them from interacting with each other to produce artifacts and wasting reaction resources. The presently preferred positions for placing these nucleotides is near the 3'-end of the primer, where the very "last" nucleotide in the primer (at the 3'-end) is standard, while the four proceeding nucleotides are chosen from the self-avoiding molecular recognition system.

To practice the instant invention with respect to a preselected target sequence, Primers FIP and BIP (FIG. 1) are chosen to complement segments of that sequence not distantly separated. Distances of 50 to 150 are most preferred presently. Primers FIP and BIP have sequences that are complementary to the sequences of the target preselected regions, following Watson-Crick pairing rules, as well known in the art. After single copying steps, the loop structure shown in FIG. 1 and repeated in FIG. 2 is generated. At this point, the practice of the instant invention diverges from the practice of LAMP as known in the art. Here the LB sequences are created, again following Watson-Crick pairing rules, as well known in the art. This may be done with standard nucleotides only in the tagged region, or more preferably with AEGIS nucleotides in the tagged region. Separately, self-avoiding molecular recognition systems may be incorporated into some or all of the single-stranded primers.

A priori, it was not clear that any loop-involving architecture would accept self-avoiding nucleotides. Accordingly, a key element in creating this invention was the demonstration, shown in Example 4, that certain self-avoiding nucleotides were in fact accepted in the loop-involving amplification architecture. The presently preferred placement of these self-avoiding nucleotides is at or near the 3'-end of the primers. Most preferably, between two and four of these nucleotides are present in the five terminal positions of these primers.

The entire value of isothermal amplification processes is the ease with which they can be used, especially in lower resource environments where expensive instruments are not available, or by personnel who need not have a degree specializing in nucleic acid analysis or a license to practice complex nucleic acid analysis. However, in those environments, sample preparation becomes an important problem. Given the simplicity of this method for creating signals, complex sample preparation becomes a severe problem.

Accordingly, a fourth level of invention is proposed. Here, low-fluorescence cellulose paper (e.g. Whatman filter paper) is modified to attach, by covalent linkages, quaternary (Q) ammonium moieties. Each of these has a permanent positive charge; thus, is not like Qiagen diethylaminoethyl supports (which are tertiary amines that lose there positive charge at high pH). The product, called Q-paper, can absorb negatively charged xNA at low salt concentrations at any pH. Q-paper is made by treating the paper, with a solution of NaOH, followed by washing and then treatment with glycidyltrimethyl ammonium chloride [Yang, F., Song, X., Yan, L. (2015). Preparation of cationic waste paper and its application in poisonous dye removal. *Water Sci. Technol.* 67, 2560-2567].

The art had taught us to expect that polycationic supports such as Q-paper would absorb nucleic acids by columbic interactions. However, once absorbed, the art taught us to expect them to not be available as templates for any amplification system and, in particular, any isothermal amplification system run at temperatures of 65° or below. Further, the art taught us to expect that the paper support would inactivate the polymerase used in this amplification process, or adsorb the primers.

Accordingly, a key element in creating this invention was the demonstration, shown in Example 2, that it was possible to introduce the Q-paper carrying the target xNA directly into the process of the instant invention, and to see products.

This led to a very simple sample preparation process combined with our product generation process. In a specific embodiment shown in Example 2, a mosquito carcass or a blood spot is placed on Q-paper supported by a blotter. Then, two drops of a mixture of detergent and $NH_3$ are added, and are soaked through the Q-paper into the blotter. Two drops of ethanol are then added on top of the sample; the ethanol is likewise soaked through the paper under the blotter. As the Q-paper is a polycation, the DNA and RNA polyanions absorb strongly to the Q-paper due to coulombic interactions. This allows the ammonia and ethanol washes to draw bile acids and other inhibitors, or pterins and other interferers, into the blotter. Ethanol, of course, is also sterilizing. A subsequent washed with water is optional. Further, both evaporate easily, generally without requiring any special step to cause that evaporation.

Example 2 applies this to two viruses that provide RNA as the analyte, Zika and chikungunya. In both cases, *Aedes aegypti* female mosquitoes infected with the relevant virus were used. To prove the presence of the virus in individual mosquitoes, viral titers were measured in the mosquito legs using TaqMan quantitative RT-PCR. The carcasses the mosquitoes were then squashed on the surfaces of Q-paper.

The infected mosquitoes were directly squished onto Q-paper, without RNA purification. Here, the process of the instant invention was used with a displaceable probe. The results are shown in FIG. 7.

A final application of the reverse displaceable probe invention is the ability to multiplex its output. Multiplexing has utility for two reasons. First, a kit for uninitiated users requires a positive control signal that assures the user that the kit is working. Second, multiple viruses are important to public health, is useful to have a kit that detects more than one of these.

The reverse displaceable probe architecture offers a solution to this. Here, different oligonucleotide sequences are used to hybridize different fluorescently tagged oligonucleotides to the 5'-prime ends of primers that target different target analytes. AEGIS nucleotides may be used to ensure clean hybridization. The complements to the fluorescently tagged oligonucleotides are then place in the detection zone, with different arrangements for the different analytes. These capture oligonucleotides are complementary to the different fluorescently tagged oligonucleotides that are displaced during the process of the instant invention (FIG. 8).

For example, and without limitation, the capture oligonucleotides may be imprinted on the surface of a solid support. By monitoring the emitted fluorescence, the process of the process of the instant invention reaction may be detected. The detection of amplification of the target DNA may be sequence-specific.

This is further distinct, and not rendered obvious, by the art. For example, Kubota teaches multiplexing, but requires that "each assimilating probe . . . employ [a] spectrally unique fluorophore that can be monitored independently." In practice, very few spectrally unique fluorophores are possible, and the human eye has difficulty distinguishing the presence any fluorophores if two or more of these are emitting light at the same lime from a single tube. This would be necessary for an assay that contains, for example, both a positive control emission and emission from a fluorophore that indicates the presence of a target analyte.

The presently preferred embodiments of the disclosed invention present the target analyte adsorbed on a Q-paper support, operate the amplification at temperatures between 60 and 70° C., most preferably at 65±1° C., and use fluorescein as the fluorescent species and Iowa Black as the quenching species.

Beneficially, the instant invention facilitates rapid detection of pathogens in the particular samples of interest here RNA viruses in trapped mosquitoes and in urine. The detection is called within 20 to 30 minutes, enabling timely management decisions. The disclosed invention is useful in many other contexts, including, but not limited to, clinical diagnostics in low resource settings, the identification of biological agents by security personnel. It should be noted that during the most recent outbreak of Zika virus in Miami-Dade County, the Center for Disease Control, which used classical methods to detect xNA target analytes, was asking pregnant women to wait 2 to 4 weeks before learning the status of their Zika infection.

EXAMPLES

In the examples below, embodiments of the strand displaceable probes are tested to assess their ability to monitor the process of the instant invention.

Preparation of Q-Paper

Quaternary ammonium modified paper (Q-paper) was made by treating the Whatman filter paper with an NaOH solution, followed by washing with water and then treatment with glycidyltrimethyl ammonium chloride, following a literature procedure [Yang, F., Song, X., Yan, L. (2015). Preparation of cationic waste paper and its application in poisonous dye removal. *Water Sci. Technol.* 67, 2560-2567 PMID: 23752389]. Tire Q-paper sheets were cut into small squares (~0.5 cm²). *Aedes aegypti* female mosquitoes were squished on each paper square. The squished carcass was treated with 100 µL of a 0.1 M aqueous NH₄OH solution. The papers were washed once with 100 µL of 50% EtOH and once with 100 µL of ddH₂O, and air dried. The paper squares, with and without target, were then placed inside instant invention mixture.

Example 1. Malaria RNA in Blood as a Target for the Process with AEGIS Components This experiment shows that the reversed LAMP architecture works with AEGIS components. The following primer sets were synthesized by solid phase phosphoramidite synthesis.

| Malaria LAMP Set 2: | | |
|---|---|---|
| Sequence | Sequence | |
| Malaria_Lamp-2_F3 | TCTGACCTATCAGCTTTTG | SEQ ID NO 1 |
| Malaria_Lamp-2_B3 | AATTCCYAYCATTCAATTRC | SEQ ID NO 2 |
| Malaria_Lamp-2_LF | CCCCGTTACCCGTCATAG | SEQ ID NO 3 |
| Malaria_Lamp-2_LB | GCAGGCGCGTAAATTACC | SEQ ID NO 4 |
| Malaria_Lamp-2_FIP | CCCTCTCCGGAATCGAACTTTT TTGTTAGGGTATTGRCCTA | SEQ ID NO 5 |
| Malaria_Lamp-2_BIP | ACCACATCTAAGGAAGGCATTT TTTCACTACCTCTCTTYTTTAG | SEQ ID NO 6 |
| Malaria_Lamp-2_LB_AEGIS_Probe | /FAM/CGPGTTTGCPCTCAPCCA TCCGTTCAPTCCGTCAPGTCAGC CCCGTTACCCGTCATAG | SEQ ID NO 7 |

| Malaria LAMP Set 3: | | |
|---|---|---|
| Sequence | Sequence | SEQ ID NO 8 |
| MalLamp-3_F3_1 | ATAAACTATRCCRACTAGG | SEQ ID NO 9 |
| MalLamp-3_B3_1 | TGTCAATCCTACTCTTGTC | SEQ ID NO 10 |
| MalLamp-3_LF_1 | CCCCAGAACCCAAAGACT | SEQ ID NO 11 |
| MalLamp-3_LB_1 | TGGACTTGCGGCTTAA | SEQ ID NO 12 |
| MalLamp-3_FIP_1 | ACTTTCTCGCTTGCGCTTTTT CCTTCAGTRCCYTATGAGAA | SEQ ID NO 13 |
| MalLamp-3_BIP_1 | ATTGACGGAAGGGCACCTTTT TTTTYCCCGTGTTGAGTC | SEQ ID NO 14 |
| MalLamp-3_LF_AEGIS_Probe | /FAM/CGPGTTTGCPCTCAPC CATCCGTTCAPTCCGTCAPGT CAGCCCCAGAACCCAAAGACT | SEQ ID NO 15 |

This AEGIS-containing quenching strand was used in an assimilating probe architecture 5'-CTGACZTGACGGAZT-GAACGGATGGZTGAGZGCAAACZCG/Dab/ SEQ ID NO 16 The following reaction conditions were used with 100 nM of the assimilating probe.

| Components (25 µL total) | Volume | Final concentration |
|---|---|---|
| 10x isothermal amplification buffer* | 2.5 µL | 1x (20 mM Tris-HCl, 10 mM (NH₄)₂SO₄, 50 mM KCl, 2 mM MgSO₄, 0.1% Tween 20; pH 8.8) |
| 10 mM dNTPs (each)* | 3.5 µL | 1.4 mM each |
| 10 mM dPTP | 1.25 µL | 0.5 mM |
| 1 mM dZTP | 1.25 µL | 0.05 mM |
| 100 mM MgSO₄* | 1.5 µL | 6 mM + mM in buffer = 8 mM |
| 10x LAMP primer mix# | 2.5 µL | 1.6 µM FIP/BIP, 0.2 µM F3/B3, 0.5 µM LB, 0.4 µM LF, 0.1 µM LF-probe, 0.15 µM Q-strand |
| Bst 2.0 warm-start (8 U/µL)* | 1 µL | 0.32U/µL |
| WS-RTx (15 U/µL)* | 0.5 µL | 0.3U/µL |
| sample (H₂for NTC) | 1 µL | 0.1, 1, and 10 pg RNA/xNA |
| H₂O | 10 µ µL | |

The samples were RNA from *Plasmodium falciparum* RNA (200 ng/µL) and xNA (500 ng/µL) in blood. RNA (R) and xNA (X) were diluted to 0.1, 1, and 10 pg/µL. As a no template control (NTC), 1 µL H₂O was used instead of sample. As a non-specific control (NSC), mosquito RNA (100 pg) was used in the sample instead of *falciparum* RNA.

Reaction mixtures were incubated at 65° C. for 65 minutes and fluorescence was detected in real-time. Results are shown in FIG. 7. As is evident from the plot, with P and Z (FIG. 5) as the AEGIS components, the fluorescent signal emerged essentially as fast as it does with completely the system with completely standard nucleotides.

Example 2—Application of the Instant Invention to Detect Viruses in Mosquitoes The assay design exploits a LAMP architecture (FIG. 1), but with two variants. First, we exploit the low noise of an AEGIS beacon to create a signal [Sheng, P. P., Yang, Z. Y., Kim, Y. M., Wu. Y. R., Tan, W. H. Benner, S. A. (2008) Design of a novel molecular beacon. Modification of the stem with artificially genetic alphabet. *Chem. Comm.* (41), 5128-5130]. This requires that the AEGIS stem regions of the beacon "map" back to their complements in the loop regions of the dumbbell.

Second, this beacon incorporated a single RNA nucleotide. This allows RNase H2 to cleave the beacon alter it has hybridized to the amplicon. This cleavage breaks the covalent bond that links the fluorescent moiety to the quencher; the stem is no longer able to keep these two together. This allows the beacon fragments to dissociate from the amplicon, a second beacon to bind and suffer cleavage. As a result, the signal is amplified. The position of the beacon binding was chosen to ensure that the duplex with the amplicon was long enough to satisfy the substrate requirements of RNase H2 and, after RNase H cleavage, and that the resulting fragment met the structure required of a LAMP primer.

As two final design features, the sample preparation procedure exploiting Q-paper was used, involving treatment with ammonium hydroxide. This lyses most growing bacteria and nearly all viruses, provided that the pH is above 11 [Salo, R. J. and Cliver, D. O., 1976. Effect of acid pH, salts, and temperature on the infectivity and physical integrity of enteroviruses. Arch. Virol. 52, 269-282.]. This is achieved by ensuring that the concentration of ammonia is greater than 100 mM, preferably 200 mM, after buffering effects of the sample is considered. This also renders the sample non-infectious. Further, the high pH disrupts through deprotonation (of G and T) all secondary structure that might be present in the pathogen xNA, and releases the RNA from any bound proteins by deprotonating lysine or arginine residues.

Primers for the Positive Control (Targeting Mosquito Ribosomal RNA)

The molecular structure/sequence of each of these primers, fluorescent and quencher probes for use process of the instant invention with target organisms are summarized in Table 1. A primer set targeting small subunit ribosomal RNA of *Aedes aegypti* species was used to evaluate the performance of the reverse displaceable probes.

| Name | Sequence (5'-3') | Type | Start Posit | End Posit | SEQ ID NO 16 |
|---|---|---|---|---|---|
| Aae-1_F3 | GGTGTAGTGT GACCTG | External primer | 2501 | 2524 | SEQ ID NO 17 |
| Aae-1_FIP | CGTGCAGCC AGAACATTTT TGCAAAATGA CATTGAGCG | Internal primer | 2260 | 2678 | SEQ ID NO 18 |
| Aae-1_LF | TCTAAGGGCA TCACGGAC | Loop primer | 2705 | 2687 | SEQ ID NO 19 |

TABLE 1

Primers targeting *Aedes aegypto* SSU rRNA.

| Aae-1_LB | AAGGGCCGGG AAATCG | Loop primer | 2777 | 2793 | SEQ ID NO 20 |
| Aae-1_BIP | CAACGCGTAT CCTTGCCTTTT TAATCCCGAC TAAATGCG | Internal primer | 2820 | 2803 | SEQ ID NO 21 |

TABLE 1-continued

Primers targeting *Aedes aegypto* SSU rRNA.

| Aae-1_B3 | GCTAGCTAAT GACCAGC | External primer | 2883 | 2866 | SEQ ID NO 22 |
| Aae-1_LF_dp5IB-FQ | IowaBlackFQ-GGGTTTGCGC TCAGCCATCC GTTCAFTCCG TCAGGTCAG TCTAAGGGCA TCACGGAC | Strand displaceable loop primer | 5656 | 5656 | SEQ ID NO 23 |
| Aae-1_LF_tailco mp3F-AM | CTGACCTGAC GGACTGAACG GATGGCTGAG CGCAAACCC-FAM | Displaced probe | | | SEQ ID NO 24 |
| Aae-1_LF_tailcap t24nt-5NH2 | NH2-C12spacer-GGG TTT GCG CTC AGC CAT CCG TT/3ddC/ | Capture probe | | | SEQ ID NO 25 |

Design of Reverse Displaceable Probes for the Instant Invention

In an embodiment to show the use of reverse displaceable probes for detection of a target analyte, the quencher strand of the reverse displaceable probe was designed to contain a primer sequence substantially complementary to a loop generated in the DNA product obtained from the SSU rRNA of the mosquito *Aedes aegypti*. This LF primer sequence is at the 3'-end of a two-part oligonucleotide, the second part being a tagging sequence that is substantially complementary to an oligonucleotide carrying a fluorescent tag at its 5'-end. The fluorescent moiety fluorescein (FAM) was conjugated to the 3'-end of the fluorescent probe. Thus, when the fluor-tagged oligonucleotide is hybridized to the LF molecule, the quencher moiety (here Iowa Black-FQ) conjugated to the 5'-end of the priming strand effectively quenches the fluorescence of the fluor-tagged oligonucleotide.

Reactions were performed in approximately 50 µL (total volume) of a reaction mixture that contained ca. 1.6 µM FIP and BIP, 0.2 µM F3 and B3, 0.5 µM LB, 0.2 µM LF, 0.4 µM LF quencher probe, and 0.3 µM fluorescent probe, 1.4 mM of each deoxynucleoside triphosphate (dNTPs), 20 mM Tris-HCl (approximately pH 8.8), 50 mM KCl, 10 mM $(NH_4)_2SO_4$, 8 mM $MgSO_4$, 0.1% Tween® 20.1 mM DTP, 16 U of Bst 2.0 WarmStart® DNA Polymerase (NEB, Ipswich, Mass.), 15 U of WarmStart® RTx Reverse Transcriptase (NEB, Ipswich, Mass.), 80 U of RNascOUT™ recombinant ribonuclease inhibitor (Thermo Fisher Scientific, Waltham, Mass.) and the square of Q-paper carrying the squished mosquito carcasses The process was carried out in 0.2 mL microtubes at 65° C. for 60 min. Samples were then analyzed by 2.5% agarose gel electrophoresis in 1×TBE buffer, followed by ethidium bromide staining, using appropriate DNA size markers (e.g., 50 bp ladder; Promega, Madison, Wis.). (FIG. 6A)

Additionally, images of fluorescence generated by reverse displaceable probes induced by blue LED light (470 nm) at room temperature were recorded through an orange filter by a cell phone camera (e.g. iPhone 6s). (FIG. 6B)

For the real-time monitoring according to the instant invention, the reactions were incubated at 65° C. for 60 min and the fluorescence signals (FAM; $\lambda_{ex}/\lambda_{em}$=495 nm/520 nm, excitation with a blue light) were measured every 30 seconds using Roche Light Cycler 480 (Roche Life Sciences, Indianapolis, Ind.). (FIG. 6C)

Capture of Displaced Probes on Solid Surface
Manual Printing

Solutions (0.5 μL) containing 100 μM (50 pmole in 0.1 M NaHCO$_3$) of oligonucleotide probes with 5'-end amino modifications (IDT, Coralville, Iowa), were manually printed on squares of cyanogen bromide-activated Whatman papers (about 2-3 cm). After printing, the squares were stored in a humidification chamber at room temperature overnight. To quench unreacted cyanate groups the paper squares were treated with a solution of 50 mM ethanolamine in 0.1 M NaHCO$_3$ (2 mL) for 1 h. Squares were then washed sequentially with deionized water (3×2 mL, 2 min), a pre-warmed (50° C.) solution of 4×-saline-sodium citrate (SSC) buffer (pH=7) containing 0.1% sodium dodecyl sulfate (2 mL, 1 min), and deionized water (3×2 mL, 2 min), followed by air-drying.

Hybridization by Capillary Transport

To demonstrate the ability of the paper-immobilized probes to detect strand displaced fluorescent probes, 20 μL of the reaction mixture was spotted on paper squares and air-dried, about 15 minutes. Squares were then washed a pre-warmed (50° C.) solution of 2×-saline-sodium citrate (SSC) buffer (pH=7) containing 0.1% sodium dodecyl sulfate (2 mL, 1 min). Air-dried paper squares were then visualized under UV (254 nm), and images were captured by a cell phone camera. (FIG. 7)

TABLE 2

Primers targeting varios pathogen RNA target analyte molecules

| Target | Fluorophore | Color Under UV (254 nm) | Excitation-Emission wavelength |
|---|---|---|---|
| Zika | FAM | Green | 495-520 nm |
| Chikungunya | HEX | Yellow | 538-555 nm |
| Dengue-1 | TAMRA | Orange | 559-583 nm |
| Common quencher | Iowa Black-FQ | — | 420-620 nm |

TABLE 3

Primers targeting various pathogen RNA target analyte molecules

| Zika set19 | Sequence (5'-3') | Type | SEQ ID NO | Start Pos | End Pos |
|---|---|---|---|---|---|
| ZV Set19_F3 | GAGACTGCTTGCCTAG | External primer | SEQ ID NO 26 | 9905 | 9920 |
| ZV Set19_B3 | CTGGGGTCTTGTCTTC | External primer | SEQ ID NO 27 | 10145 | 10130 |
| ZV Set19_LF | CAGTTGGAACCCAGTCAAC | Loop primer | SEQ ID NO 28 | 10028 | 10010 |
| ZV Set19_LB | GTGGAACAGAGTGTGGATTG | Loop primer | SEQ ID NO 29 | 10093 | 10112 |
| ZV Set19_FIP | CCATGGATTGACCAGGTAGTTTTTT CGACTGATGCCAATG | Internal primer | SEQ ID NO 30 | 9974 | 10053 |
| ZV Set19_BIP | ACCACTGARGACATGCTTGTTTTTC ATGTGGTCGTTYTCC | Internal primer | SEQ ID NO 31 | 10070 | 10129 |
| ZV Set19_LB_NatTail | Iowa Black FQ - CGGGTTTGCGCTCAGCCATCCGTTC AGTCCGTCAGGTCAG-GTGGAACAGAGTGTGGATTG | Strand displaced probe | SEQ ID NO 32 | 10093 | 10112 |
| Flourescent oligo | CTGACCTGACGGACTGAACGGATG GCTGAGCGCAAACCCG-FAM | Displaced probe | SEQ ID NO 33 | | |

| Chikungunya set10 | Sequence (5'-3') | Type | SEQ ID NO 34 | Start Pos | End Pos |
|---|---|---|---|---|---|
| Chik10_F3 | CGTCAACGTACTCCTAAC | External primer | SEQ ID NO 35 | 2891 | 2908 |
| Chik10_B3 | ACGTTGGCTTTRTTTTGG | External primer | SEQ ID NO 36 | 3094 | 3077 |
| Chik10_LF | AGCGGTCTTTATCCACGGG | Loop primer | SEQ ID NO 37 | 2968 | 2951 |
| Chik10_LB | AYGCATCRATAATGGCGGG | Loop primer | SEQ ID NO 38 | 3025 | 3043 |
| Chik10_FIP | GAAGTTTCCTTTCGGTGGGTTTT TGGAAGACACTYTCYGG | Internal primer | SEQ ID NO 39 | 2932 | 2993 |
| Chik10_BIP | AAGGAGTGGGAGGTGGATTTTT TCAYTTGGTGACTGCAG | Internal primer | SEQ ID NO 40 | 3006 | 3063 |
| Chik10_LF_NatTail | Iowa Black FQ - CGGGTTTGCGCTCAGCCATCCGT TCAGTCCGTCAGGTCAG-AGCGTCTTTATCCACGGG | Strand displaced probe | SEQ ID NO 41 | 2968 | 2951 |
| Flourescent oligo | CTGACCTGACGGACTGAACGGA TGGCTGAGCGCAAACCCG-HEX | Displaced probe | SEQ ID NO 42 | | |

| Dengue-1 set5 | Sequence (5'-3') | Type | SEQ ID NO 43 | Start Pos | End Pos |
|---|---|---|---|---|---|
| Den1-5_F3 | ACAGCTCTGAATGAYATGG | External primer | SEQ ID NO 44 | 9583 | 9601 |
| Den1-5_B3 | GCGTTTCTCTCAGGC | External primer | SEQ ID NO 45 | 9803 | 9788 |
| Den1-5_LF | CACTTGYTGCCARTCATTCC | Loop primer | SEQ ID NO 46 | 9666 | 9647 |

TABLE 3-continued

Primers targeting various pathogen RNA target analyte molecules

| | | | | | |
|---|---|---|---|---|---|
| Den1-5_LB | CCATGCCGYAACCAAG | Loop primer | SEQ ID NO 47 | 9727 | 9742 |
| Den1-5_FIP | CTGGTGGAARTGGTGTGAAT TTTTGGGAACCTTCAAAAGG | Internal primer | SEQ ID NO 48 | 9628 | 9693 |
| Den1-5_BIP | GAAGGAYGGGAGGGAAATA GTTTTTTTAGCCCTRCCCACA AG | Internal primer | SEQ ID NO 49 | 9702 | 9763 |
| Den1-5_LBNatTail | Iowa Black FQ - CGGGTTTGCGCTACAGCCATC CGTTCAGTCCGTCAGGTCAG-CCATGCCGYAACCAAG | Strand displaceable probe | SEQ ID NO 50 | 9727 | 9742 |
| Fluorescent oligo | CTGACCTGACGGACTGAACG GATGGCTGAGCGCAAACCCG-TAMRA | Displaced probe | SEQ ID NO 51 | | |

Example 3. Norovirus Detection in Feces

Murine norovirus (MNV) in contaminated mouse stools was used fs a sample, with the target being the RNA viral sequence. As a consequence, as is always the case for an RNA target, a reverse transcriptase was used.

AEGIS-LAMP was tested with a molecular beacon probe on standardized amounts of plasmid DNA containing the noroviral sequence. LAMP reaction mixtures included $10^6$ copies of plasmid DNA in the presence or absence of thermostable RNase H2 (IDT). With DNA template. LAMP produced the expected ladder of DNA concatemers (FIG. 10). In the negative control lacking plasmid, a faint band was observed at ~40 bp; this was assigned to the primers themselves that, despite their single stranded state, bound to ethidium bromide stain. Further, we detected the LAMP amplicons using molecular beacons (MBs) present in situ during the LAMP (45 min, FIG. 11), after cooling to room temperature to re-anneal any uncleaved or unbound beacon. Here, distinguishing samples containing noroviral target from negative controls was easily done by eye.

For calibrating the amount of extractable norovirus RNA in stools, DNA samples were then used to provide a standard curve (FIG. 12) to estimate the "effective" amount of extractable RNA in stool samples. The term "effective" is used here to indicate that (a) the Trizol extraction procedure need not be 100% yielding and (b) LAMP and RT-LAMP might have different efficiencies. The amount of plasmid-derived noroviral DNA is assumed to be known, within only the experimental error associated with a UV absorbance used to quantitate it. Given these assumptions, ~1000 MNV-1 copies were present in a typical milligram of stool. The amounts are greater if the RT-LAMP or extraction efficiencies are lower, but are expect to scale uniformly across all samples.

The impact of RNase H2 on the amount of signal generated using beacons containing a single ribonucleotides linker, as before. To determine if RNase nicking enhances the overall signal, parallel LAMPs were performed with and without thermostable RNase H2 (FIG. 14). At 65° C., all beacons "glow", as AEGIS stem does not hold the beacon closed at this temperature to bring the fluorophore and the quencher into proximity. The glow from the intact beacon goes away if it has not found a complement to hybridize as the temperature is lowered. Thus, by this mechanism, a beacon glows only if it is bound to an amplicon at the lower temperature.

In contrast, RNase H2 cleaves the oligonucleotide that covalently links the fluorophore and the quencher. The AEGIS stem is too short to hold together the cleaved fragments. Hence, the beacon fragments glow if at any point in the LAMP, the beacon has been hybridized to an amplicon long enough for RNase H2 to find and cleave it. This allows the entire glow to be equal to the sum of the number of beacons presently bound to amplicon added to the beacons that once were bound to the amplicon.

Further, once cleaved, the beacon fragment itself can be a LAMP primer. Therefore, it can increase the overall "end point" glow simply by increasing the number of amplicons. This is, of course, provided only if the LAMP has not been run past the point where all primers and all beacons have been consumed.

Finally, although the fluorophore and quencher are more distant in the opened beacon than in the hairpin, they are not freely separated. Thus, the fluorophore in the opened, uncleaved beacon, might still be partially quenched. This is another mechanism by which the RNase H2 will generate enhanced signal.

When experiments were run in duplicate, the fluorescence of the signal obtained with RNase H2 was ~60% stronger than the signal obtained without it (FIG. 13, FIG. 14). This quantitative difference could even be observed by eye in tubes illuminated at 470 nm.

To determine the sensitivity of the assay, varying amounts of viral RNA (1000 copies down to 5 copies per reaction) Trizol-extracted from mouse stools and calibrated by comparison with a standard curve from plasmid noroviral DNA were introduced into the LAMP assay. The limit of detection (LOD) of the assay was found to be ~10 viral RNA copies/reaction, as determined by both gel electrophoresis and AEGIS-MB signaling analysis (data not shown). These results were compared with results obtained using a LAMP primer set reported by [Hanaki, K., Ike, F., Kajita, A., Yasuno, W., Yanagiba, M., Goto, M., Sakai, K., Ami, Y. and Kyuwa, S., 2014. Detection of murine norovirus by reverse transcription loop-mediated isothermal amplification. J. Virol. Methods 204, 17-24.]. This targeted a different region (the junction between ORF 1 and 2), had only 5 LAMP primers, had no AEGIS the primers, and signaled using hydroxynaphthol blue. They had 2 outer primers (F3/B3), 2 internal primers (FIP/BIP) and 1 backward loop primer (LB). The LOD for their system was determined to be only ~100 copies/reaction (FIG. 16 to FIG. 19), identical to their published report.

Closed beacon-dependent assays were then done directly on stool samples without viral RNA purification, where background nucleic acid of unknown sequence is abundant. Here, suspensions of stool (2% and 1% w/v, estimated to contain 20 and 10 viruses) in Tris buffer (10 mM, pH 7.5, 5 µL) were treated with equal volumes of ammonium hydroxide (30 mM, final pH 10.2). To reduce the activity of RNase that might be present in the stool, DTT was added to the ammonia solution.

All of this mixture (10 μL) was then added to a solution of RT-LAMP components (15 μL). In parallel, a size exclusion centrifugation filter (100 kDa cut-off limit) was used to determine if the stool contained material that inhibited LAMP.

Both without and with centrifugation, LAMP generated amplicons from MNV-1 infected stool samples. These were detectable both by gel (FIG. 16) and by beacons exhibited fluorescence whereas no signal amplification was observed in mock-infected cases. (FIG. 5 17). No inhibitors were evident at these amounts of stool. Separately, it had been observed that when higher concentrations of mock-inoculated stool samples (20%, 10% or 5%) were used in LAMP reaction, MBs exhibited non-specific fluorescence. Therefore, 2% stool was the highest amount used.

For DNA standards, full-length MNV-1 plasmid DNA (designated as pSPMNV-1.CW3), MNV-1 infected and mock-inoculated mice stool samples (GenBank accession no. KC-782764) were all obtained by previous procedures [Zhu, S., Regev, D., Watanabe, M., Hickman, D., Moussatche, N., Jesus, D. M., Kahan, S. M., Napthine, S., Brierley, I., Hunter, R. N., Devabhaktuni, D., Jones, M. K. and Karst, S. M., 2013. Identification of Immune and Viral Correlates of Norovirus Protective Immunity through Comparative Study of Intra-Cluster Norovirus Strains. PLoS Pathog. 9, e1003592.]. Primers and molecular beacons were designed by analysis of multiple sequence alignments (MSAs) of virus homolog families built from public databases to identify regions within those viral genomes that have a level of sequence divergence that allows viral targets to be distinguished, but not so much to prevent detecting viruses that are divergently evolving. A BLAST search then was used to ensure that primer and probe sequences are not closely similar to sequences in both the NCBI RN A virus database and the NCBI human genome database.

LAMP primers containing only standard nucleotides and RNase H2 were from Integrated DNA Technologies (IDT, Coralville, Iowa). FIP and BIP primers and molecular beacon containing artificial AEGIS nucleotides were synthesized on ABI 394 and ABI 3900 synthesizers at Firebird Biomolecular Sciences LLC and RP-HPLC purified (Table 1). RNase H2 cleavable AEGIS molecular beacons were designed to have single ribonucleotide linkage on the 19th base position. AEGIS molecular beacon was labeled with a fluorophore, FAM, at the 5'-end, and a quencher, DABCYL, at 3'-end and dC:dG pair in its stem was replaced by dZ:dP pair.

Bst 2.0 WarmStart DNA polymerase and WarmStart RTx reverse transcriptase were purchased from NEB (Ipswich, Mass.). EvaGreen dye (20× in $H_2O$) was purchased from Biotium (Hayward, Calif.).

MNV-1 RNA Extraction.

Viral RNA was purified using the Trizol method (Life Technologies) and subsequent column purification. Briefly, 30-50 mg of MNV-1 infected stool samples were suspended in Trizol reagent (1 mL, Invitrogen, Carlsbad, Calif.). Samples were centrifuged at 10,000×g for 2 min, and the supernatant was purified using Direct-zol RNA MiniPrep Kit (Zymo Research, Irvine, Calif.) and eluted in nuclease-free $H_2O$ (50 μL), aliquoted and stored at −80° C. until use.

Virol Load Determination by Real-Time RT-LAMP.

To determine the copy number of the viral RNA in the sample, serial dilutions of the MNV-1 plasmid DNA was prepared to generate a standard curve. LAMP was performed in a reaction mixture (25 μL) containing plasmid DNA standard (1 μL, $10^7$ down to 10 copies), Ae-FIP and Ae-BIP (1.6 μM each) (FIG. 1), F3 and B3 (0.2 μM each), LB and LF (0.4 μM each), dNTPs (1.4 mM each), $MgSO_4$ (4 mM), dPTP (0.5 mM), dZTP (0.05 mM), Bst 2.0 WarmStart DNA polymerase (8 Units) and EvaGreen dye (0.4×) in LAMP buffer (20 mM Tris-HCl pH 8.8.2 mM $MgSO_4$, 50 mM KCl, 10 mM $(NH_4)_2SO_4$, 0.1% Tween-20).

The reaction mixture for RT-LAMP was identical to those described above for LAMP except that Trizol-purified RNA (1 μL, with up to $10^3$-fold dilutions) was used as template and WarmStart RTx Reverse Transcriptase (7.5 U) was included in the reaction mixture. For the negative controls in LAMP, templates were substituted with nuclease free water. The samples were incubated at 65° C. for 45 min using a Roche Light Cycler 480 with continuous fluorescence monitoring.

AEGIS LAMP with MB for Detection of MNV-1 Plasmid DNA.

AE-LAMP was performed in reaction mixture (25 μL) containing plasmid standard (1 μL, $10^6$ copies), Ae-FIP and Ae-BIP (1.6 μM each), F3 and B3 (0.2 μM each), LB and Ae-LF beacon (0.4 μM each), dNTPs (1.4 mM each), $MgSO_4$ (4 mM), dPTP (0.5 mM), dZTP (0.05 mM), Bst 2.0 WarmStart DNA polymerase (8 Units), with/without RNAseH2 (60 mU) in LAMP buffer (20 mM Tris-HCl pH

TABLE

LAMP primers and molecular beacon used for MNV-1 detection. P and Z are AEGIS components. The "rC" is the site of nicking in the RNase H-nicking AEGIS beacons.

| Name | Sequence (5'-3') | Length | Genome position | SEQ ID |
|---|---|---|---|---|
| MNV-1 LAMP_F3 | TATGGCCTGGATCTGG | 16 | 1196-1211 | SEQ ID NO 52 |
| MNV-1 LAMP_B3 | GTTGGTGGTTCCAGTG | 16 | 1403-1418 | SEQ ID NO 53 |
| MNV-1 LAMP_LB | CCCTTGATGAGGAGGAGC | 18 | 1342-1359 | SEQ ID NO 54 |
| MNV-1 LAMP_LF | CTTAATGATGGCCTGCTCC | 19 | 1250-1268 | SEQ ID NO 55 |
| MNV-1 LAMP_AeLF_Beacon | FAM-CPTGZGCTCATTCTTAATGATGGCrCTGCTCCCPCAZG-dabcyl | 37 | 1250-1274 | SEQ ID NO 56 |
| MNV-1 LAMP_AeFIP (F1c-F2) | CCGTGAGTTGGTTCTCCATPTPTCAGCCCTCTTATCCAAC | 40 | 1282-1299, 1231-1247 | SEQ ID NO 57 |
| MNV-1 LAMP_AeBIP (B1c-F2) | GCAGGGGCTGAATTCCTPTPTTCGATCTTGCGGACTC | 38 | 1320-1336, 1362-1377 | SEQ ID NO 58 |

8.8.2 mM MgSO$_4$, 50 mM KCl, 10 mM (NH$_4$)$_2$SO$_4$, 0.1% Tween-20). For the negative controls in LAMP, templates were substituted with nuclease free water. The samples were placed in a thermocycler and incubated at 65° C. for 45 min. LAMP amplicons (5 µL) were run on 2.5% TBE-agarose gel for visualization. Additionally, images of fluorescence generated by the molecular beacons induced by blue LED light (470 nm) at room temperature were recorded through an orange filler by a digital camera.

AEGIS RT-LAMP with Trizol Purified MNV-1 RNA.

AE-RT-LAMP was performed in a reaction mixture (25 µL) containing RNA extract (1 µL, 10$^3$ copies), Ae-FIP and Ae-BIP (1.6 µM each), F3 and B3 (0.2 µM each), LB and Ae-LF beacon (0.4 µM each), dNTPs (1.4 mM each), MgSO$_4$ (4 mM), dPTP (0.5 mM), dZTP (0.05 mM), Bst 2.0 WarmStart DNA polymerase (8 Units), WarmStart RTx Reverse Transcriptase (7.5 Units) with/without RNase H2 (60 mUnits) in LAMP buffer (20 mM Tris-HCl pH 8.8.2 mM MgSO$_4$, 50 mM KCl, 10 mM (NH$_4$)$_2$SO$_4$, 0.1% Tween-20). For the negative controls in RT-LAMP, templates were substituted with nuclease free water. The samples were placed in a thermocycler and incubated at 65° C. for 45 min. LAMP amplicons (5 µL) were run on 2.5% TBE-agarose gel for visualization. Additionally, images of fluorescence generated by the molecular beacons induced by blue LED light (470 nm) at room temperature were recorded through an orange filter by a digital camera.

Thermal profiles were recorded as follows: Mixtures were first denatured at 80° C. for 2 min, the temperature was then decreased in a rate 0.01° C./s from 80° C. to 25° C., with fluorescence continuously measured using Roche Light Cycler 480.

amplicons (5 µL) were run on 2.5% TBE-agarose gel for visualization. Additionally, images of fluorescence generated by the molecular beacons induced by blue LED light (470 nm) at room temperature were recorded through an orange filter by a digital camera.

AEGIS RT-LAMP of MNV-1 RNA without Purification.

MNV-1 infected stool suspensions (5 µL, 2% and 1% w/v in 10 mM Tris-HCl pH 7.5) were mixed with "Windex", an alkaline lysis buffer (5 µL, 30 mM NH$_4$OH, 20 mM DTT, pH 10.2). Samples were heated to 65° C. for 5 min before mixed with RT-LAMP components (15 µL). Samples were run at 65° C., for 45 min and amplicons (5 µL) were resolved on 2.5% TAE agarose gels.

As an alternative protocol, MNV-1 infected stool suspension (500 µL, 10% in 10 mM Tris-HCl pH 7.5) was first centrifuged at 10,000×g for 2 min and supernatant was placed into 0.5 mL centrifugal filters (100 kDa cut-off, Amicon Ultra, EMD Millipore) and washed/concentrated twice with Tris-HCl buffer (500 µL, 10 mM pH 7.5) by centrifugation at 10,000×g for 2 min where the solution clears out indicating the removal of LAMP inhibitory components in stool.

Example 4. Using Self-Avoiding Molecular Recognition Systems

Here, the target was synthetic DNA sequences from Powasson virus (PV). The primers were as follows, where the nucleotides with an asterix (*) were self-avoiding forms of the indicated nucleotide, as shown in FIG. 6.

| Name | Sequence | Type | SEQ ID NO |
|---|---|---|---|
| PV-3_F3 | GA*GA*CCCA*A*A*A*CCA*GA | F3 | SEQ ID NO 59 |
| PV-3_FIP | CA*GCA*A*CT*GT*CCCA*A*A*GC GCCT*T*GA*A*CA*GGA*CT*G | FIP | SEQ ID NO 60 |
| PV-3_LF tail1-5dabcyl | dabcyl-TGGGTTTPCGCTCAPCCATCCGTTCAGTCCPT CAGGTCAG GCCA*GCT*T*CT*GT*CA*T*CG | LF-tail | SEQ ID NO 61 |
| tail1-comp3FAM | CTGACCTGAZGGACTGAACGGATGGZTGAG CGZAAACCCA-FAM | tail comp | SEQ ID NO 62 |
| PV-3_LF | GCCA*GCT*T*CT*GT*CAT*CG | LF | SEQ ID NO 63 |
| PV-3_LB | CT*T*GCGGA*A*T*GGCT*GG | LB | SEQ ID NO 64 |
| PV-3_BIP | GGT*GGA*CCA*T*GCCCA* A*A*GCCCCA*T*A*GGCT*T*C* | BIP | SEQ ID NO 65 |
| PV-3_B3 | CCT*T*CT*A*GCT*CCCT*GG | B3 | SEQ ID NO 66 |

LOD of AEGIS RT-LAMP with Trizol Purified MNV-1 RNA.

AE-RT-LAMP was performed in a reaction mixture (25 µL) containing RNA extract (1 µL, 10$^3$ down to 5 copies), Ae-FIP and Ae-BIP (1.6 µM each), F3 and B3 (0.2 µM each), LB and Ae-LF beacon (0.4 µM each), dNTPs (1.4 mM each), MgSO$_4$ (4 mM), dPTP (0.5 mM), dZTP (0.05 mM), Bst 2.0 WarmStart DNA polymerase (8 Units), WarmStart RTx Reverse Transcriptase (7.5 Units), RNAseH2 (60 mUnits) in LAMP buffer (20 mM Tris-HCl pH 8.8.2 mM MgSO$_4$, 50 mM KCl, 10 mM (NH$_4$)$_2$SO$_4$, 0.1% Tween-20). For the negative controls in RT-LAMP, templates were either substituted with nuclease free water or Trizol purified mock-inoculated stool samples. The samples were placed in a thermocycler and incubated at 65° C. for 45 min. LAMP The experiments were run as follows:

| Primer concentrations: | | | | |
|---|---|---|---|---|
| Name | Extinction coeff | Stock concentration | 10X LAMP primer mix (100 µL) | Concentration in 1X LAMP |
| PV-3_F3 | 161000 | 115 µM | 1.7 µL | 0.2 µM |
| PV-3_FIP | 323200 | 76 µM | 21 µL | 1.6 µM |
| PV-3_LF | 151100 | 268 µM | 1.5 µL | 0.4 µM |
| PV-3_LB | 148200 | 192 µM | 2.6 µL | 0.5 µM |
| PV-3_BIP | 289400 | 89 µM | 17.9 µL | 1.6 µM |
| PV-3_B3 | 134100 | 173 µM | 1.1 µL | 0.2 µM |

-continued

| | Primer concentrations: | | | |
|---|---|---|---|---|
| Name | Extinction coeff | Stock concentration | 10X LAMP primer mix (100 μL) | Concentration in 1X LAMP |
| PV-3_LF-tail1-5dabcyl | 528744 | 99 μM | 2 μL | 200 μM |
| Trail1-comp3FAM | 404900 | 147 μM | 0.7 μL | 100 μM |
| | | | 51.5 μL H₂O | |

| Components (25 μL total) | Volume | Final |
|---|---|---|
| 10X isothermal amplification buffer | 2.5 μL | 1X |
| 10 mM dNTPs with dUTP | 3.5 μL | 1.4 mM |
| 100 mM MgSO$_4$ | 1.5 μL | 1.6 μM FIP/BIP, 0.2 μM F3/B3, 0.5 μM LB, 0.4 μM LF, 200 nM LF-51BFQ, 100 nM tail-3FAM |
| 10 mM dPTP | 1.25 μL | 0.5 mM |
| 1 mM dZTP | 1.25 μL | 0.05 mM |
| Bst 2.0 warm-start (8 U/μL) | 1 μL | 0.32 U/μL |
| Antarctic UDG (1 U/μL) | 0.5 μL | 0.4 U/μL |
| DNA template (1 nM, 10$^6$ to 5 copies) (or H₂O for NTC) | 1 μL | 10$^6$ copies per reaction |
| H₂O | 10 μL | |

1000 copies of target were detected in 80 min with self-avoiding nucleotides as specified in the primers, and AEGIS on the displaced probe. This can be compared with standard primers, where 1000 copies were detected in 50 min (FIG. 20).

What is claimed is:

1. A method for synthesizing multiple concatamers of a nucleic acid that incorporate sequences from a DNA target analyte to detect a target analyte, said process comprising:
    (A) providing a template that has six regions, in the following order from the 3'-end to the 5'-end, termed F3c, F2c, F1c, B1, B2, and B3,
    (B) providing an external primer, termed F3, that is substantially Watson-Crick complementary to F3c,
    (C) providing a first internal primer that has two regions, one F1c towards its 5'-end and the other F2 towards its 3'-end, where the two regions are joined by a linking oligonucleotide, and where F1c is substantially Watson-Crick complementary to F1 and F2 is substantially Watson-Crick complementary to F2c,
    wherein polymerase-catalyzed extension of said first internal primer generates a first copy that comprises F1c, F2, F1, B1c, B2c, and B3c in the 5'- to 3' direction, wherein F1c is substantially Watson-Crick complementary to F1, F2 is substantially Watson-Crick complementary to F2c, F1 is substantially Watson-Crick complementary to F1c, B1c is substantially Watson-Crick complementary to B1, B2c is substantially Watson-Crick complementary to B2, and B3c is substantially Watson-Crick complementary to B3, and then
    (D) providing a second external primer, termed B3, which is substantially Watson-Crick complementary to B3c and
    (E) providing a second internal primer that has two regions, one B1c towards its 5'-end and the other B2 towards its 3'-end, where the two regions are joined by a linking oligonucleotide, and where B1c is substantially Watson-Crick complementary to B1 and B2 is substantially Watson-Crick complementary to B2c,
    wherein polymerase-catalyzed extension of said second internal primer generates a second copy that comprises B1c, B2, B1, F1c, F2c, and F1 in the 5'- to 3' direction, said second copy can form a structure having two loops, and further comprising
    (F) a tagged primer that is a DNA molecule comprising two regions, the first tag region carrying a fluorescence quenching moiety at or near its 5'-end and the second tag region substantially Watson-Crick complementary to a region between B1 and B2 or a region between F1 and F2, and
    (G) a displaceable probe that is a DNA molecule having a fluorescent moiety at or near its 3'-end, said displaceable probe being substantially Watson-Crick complementary to the first tag region.

2. The process of claim 1, wherein a reverse transcriptase is included, and the target analyte is an RNA molecule.

3. The process of claim 1, wherein said fluorescence quenching moiety is selected from the group consisting of Iowa Black-FQ, DABCYL, TAMRA, and Black Hole Quencher.

4. The process of claim 1, wherein said fluorescent moiety is selected from the group consisting of FAM, HEX, TET, TAMRA, Cy3, and Cy5.

5. The process of claim 1, wherein said polymerase is Bst 2.0 WarmStart® DNA Polymerase.

6. The process of claim 1, wherein said incubation temperature is 60-70° C.

7. The process of claim 1, wherein said displaceable probe, after being released from its hybrid complex with said first tag region, hybridizes to an immobilized complementary oligonucleotide.

8. The process of claim 1, wherein said displaceable probe and said tagged primer hybridize to form 30-40 base pairs.

9. The process of claim 1, where the analyte is presented immobilized on a matrix with quaternary ammonium salts.

10. The process of claim 1, where the analyte is presented in a sample of feces, insect, or blood.

11. The process of claim 1, wherein one or more of the nucleotides within said tagged primer and probe are selected from the nucleotide analogs shown in FIG. 5.

12. The process of claim 11, wherein a reverse transcriptase is included, and the target analyte is an RNA molecule.

13. The process of claim 11, wherein said fluorescence quenching moiety is selected from the group consisting of Iowa Black-FQ, DABCYL, TAMRA, and Black Hole Quencher.

14. The process of claim 11, wherein said fluorescent moiety is selected from the group consisting of FAM, HEX, TET, TAMRA, Cy3, and Cy5.

15. The process of claim 11, wherein said polymerase is Bst 2.0 WarmStart® DNA Polymerase.

16. The process of claim 11, wherein said incubation temperature is 60-70° C.

17. The process of claim 11, wherein said displaceable probe, after being released from its hybrid complex with said tagged primer, hybridizes to an immobilized complementary oligonucleotide.

18. The process of claim 11, wherein said displaceable probe and tagged primer hybridize to form 30-40 base pairs.

19. The process of claim 11, where the analyte is presented immobilized on a matrix with quaternary ammonium salts.

20. The process of claim 11, where the analyte is presented in a sample of feces, insect, or blood.

21. The process of claim 1, wherein one or more of the nucleotides within said primers are selected from the nucleotide analogs shown in FIG. 6.

22. The process of claim 21, wherein a reverse transcriptase is included, and the target analyte is an RNA molecule.

23. The process of claim 21, wherein said fluorescence quenching moiety is selected from the group consisting of Iowa Black-FQ, DABCYL, TAMRA, and Black Hole Quencher.

24. The process of claim 21, wherein said fluorescent moiety is selected from the group consisting of FAM, HEX, TET, TAMRA, Cy3, and Cy5.

25. The process of claim 21, wherein said polymerase is Bst 2.0 WarmStart® DNA Polymerase.

26. The process of claim 21, wherein said incubation temperature is 60-70° C.

27. The process of claim 21, wherein said displaceable probe, after being released from its hybrid complex with said tagged primer, hybridizes to an immobilized complementary oligonucleotide.

28. The process of claim 21, wherein said displaceable probe and tagged primer hybridize to form 30-40 base pairs.

29. The process of claim 21, where the analyte is presented immobilized on a matrix with quaternary ammonium salts.

30. The process of claim 21, where the analyte is presented in a sample of feces, insect, or blood.

31. The process of claim 1, wherein one or more of the nucleotides within said tagged primer and probe are selected from the nucleotide analogs shown in FIG. 5, and wherein one or more of the nucleotides within said primers are selected from the nucleotide analogs shown in FIG. 6.

32. The process of claim 31, wherein a reverse transcriptase is included, and the target analyte is an RNA molecule.

33. The process of claim 31, wherein said fluorescence quenching moiety is selected from the group consisting of Iowa Black-FQ, DABCYL, TAMRA, and Black Hole Quencher.

34. The process of claim 31, wherein said fluorescent moiety is selected from the group consisting of FAM, HEX, TET, TAMRA, Cy3, and Cy5.

35. The process of claim 31, wherein said polymerase is Bst 2.0 WarmStart® DNA Polymerase.

36. The process of claim 31, wherein said incubation temperature is 60-70° C.

37. The process of claim 31, wherein said displaceable probe, after being released from its hybrid complex with said tagged primer, hybridizes to an immobilized complementary oligonucleotide.

38. The process of claim 31, wherein said displaceable probe and tagged primer hybridize to form 30-40 base pairs.

39. The process of claim 31, where the analyte is presented immobilized on a matrix with quaternary ammonium salts.

40. The process of claim 31, where the analyte is presented in a sample of feces, insect, or blood.

* * * * *